(12) United States Patent
Faarbaek et al.

(10) Patent No.: US 11,805,970 B2
(45) Date of Patent: Nov. 7, 2023

(54) THREE-DIMENSIONAL ADHESIVE DEVICE HAVING A MICROELECTRONIC SYSTEM EMBEDDED THEREIN

(71) Applicant: BRAEMAR MANUFACTURING, LLC, Eagan, MN (US)

(72) Inventors: Susanne Holm Faarbaek, Vaerloese (DK); Karsten Hoppe, Copenhagen (DK); Peter Boman Samuelsen, Rungsted Kyst (DK); Jens Branebjerg, Hoersholm (DK)

(73) Assignee: Braemar Manufacturing, LLC, Eagan, MN (US)

( * ) Notice: Subject to any disclaimer, the term of this patent is extended or adjusted under 35 U.S.C. 154(b) by 0 days.

(21) Appl. No.: 16/291,339

(22) Filed: Mar. 4, 2019

(65) Prior Publication Data

US 2019/0374163 A1    Dec. 12, 2019

Related U.S. Application Data

(63) Continuation of application No. 11/886,032, filed as application No. PCT/DK2006/050006 on Mar. 9, 2006, now abandoned.

(30) Foreign Application Priority Data

Mar. 9, 2005   (DK) .......................... PA 2005 00354
Dec. 9, 2005   (DK) .......................... PA 2005 01748

(51) Int. Cl.
*A61B 5/00*    (2006.01)
*A61B 5/259*   (2021.01)
(Continued)

(52) U.S. Cl.
CPC ........ *A61B 5/68335* (2017.08); *A61B 5/0002* (2013.01); *A61B 5/259* (2021.01);
(Continued)

(58) Field of Classification Search
CPC .............. A61B 5/68335; A61B 5/0002; A61B 5/04087; A61B 5/411; A61B 5/6833;
(Continued)

(56) References Cited

U.S. PATENT DOCUMENTS

| 5,409,472 A | 4/1995 | Rawlings |
| 5,634,468 A | 6/1997 | Platt |

(Continued)

*Primary Examiner* — Lynsey C Eiseman
*Assistant Examiner* — Jessandra F Hough

(57) ABSTRACT

A three-dimensional adhesive device to be attached to the body surface of a mammal including a microelectronic sensing system. The system includes (a) a three-dimensional adhesive body made of a pressure sensitive adhesive having an upper surface and a bottom surface; (b) a microelectronic system embedded in the body of the pressure sensitive adhesive; (c) one or more cover layer(s) attached to the upper surface; and (d) optionally a release liner releasably attached to the bottom surface. Suitably the microelectronic system is capable of sensing physical input such as pressure, vibration, sound, electrical activity (e.g. from muscle activity), tension, blood-flow, moisture, temperature, enzyme activity, bacteria, pH, blood sugar, conductivity, resistance, capacitance, inductance or other chemical, biochemical, biological, mechanical or electrical purposes.

19 Claims, 7 Drawing Sheets

(51) Int. Cl.
*A61B 5/145* (2006.01)
*A61B 5/02* (2006.01)
*A61B 5/024* (2006.01)
*A61B 5/291* (2021.01)
*A61B 5/296* (2021.01)

(52) U.S. Cl.
CPC ............ *A61B 5/411* (2013.01); *A61B 5/6833* (2013.01); *A61B 5/02* (2013.01); *A61B 5/024* (2013.01); *A61B 5/14532* (2013.01); *A61B 5/14539* (2013.01); *A61B 5/14542* (2013.01); *A61B 5/14546* (2013.01); *A61B 5/291* (2021.01); *A61B 5/296* (2021.01); *A61B 2560/0412* (2013.01); *A61B 2562/08* (2013.01); *Y10T 29/49002* (2015.01); *Y10T 428/14* (2015.01)

(58) Field of Classification Search
CPC ......... A61B 5/02; A61B 5/024; A61B 5/0478; A61B 5/0492; A61B 5/14532; A61B 5/14539; A61B 5/14542; A61B 5/145646; A61B 2560/0412; A61B 2562/08; A61B 5/68355; A61B 5/259; A61B 5/296; A61B 5/291; A61B 5/14546; Y10T 428/14; Y10T 29/49002
See application file for complete search history.

(56) References Cited

U.S. PATENT DOCUMENTS

| | | | |
|---|---|---|---|
| 6,117,077 | A | 9/2000 | Del Mar |
| 6,295,463 | B1* | 9/2001 | Stenzler ............ A61B 5/14542 600/386 |
| 7,206,630 | B1 | 4/2007 | Tarler |
| 2002/0180605 | A1* | 12/2002 | Ozguz ................ H01L 21/6836 340/573.1 |
| 2003/0083559 | A1 | 5/2003 | Thompson |
| 2004/0015194 | A1 | 1/2004 | Ransbury |
| 2004/0180391 | A1 | 9/2004 | Gratzl |
| 2005/0245839 | A1* | 11/2005 | Stivoric ............ A61B 5/6804 600/549 |
| 2006/0173087 | A1 | 8/2006 | Hyde |

* cited by examiner

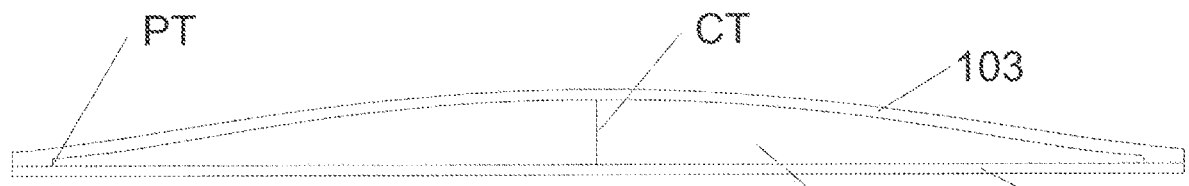
Fig.1
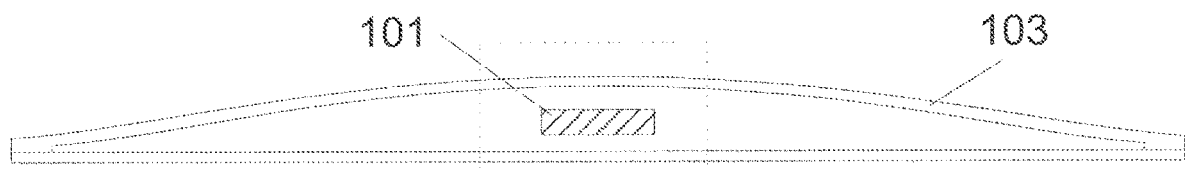
Fig.2
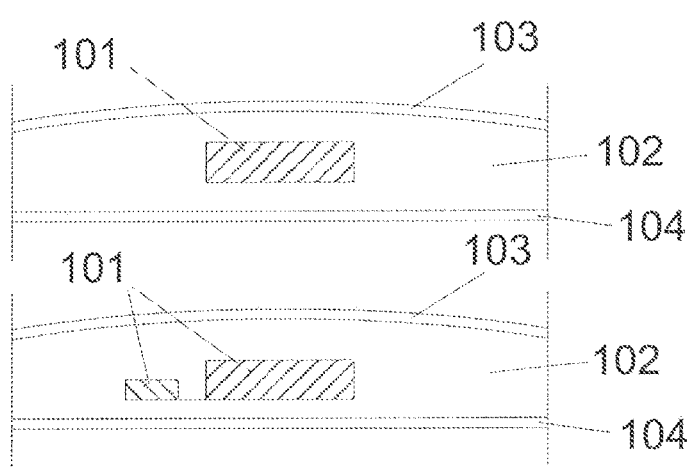
Fig.3
Fig.4
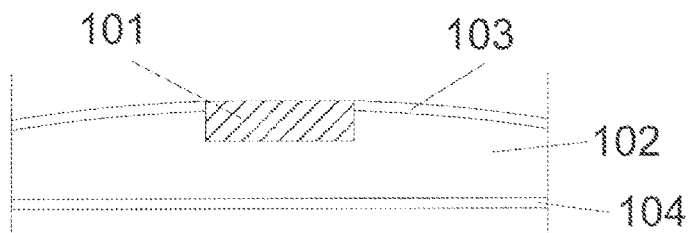
Fig.5
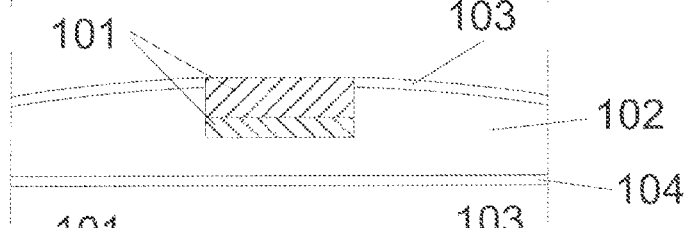
Fig.6
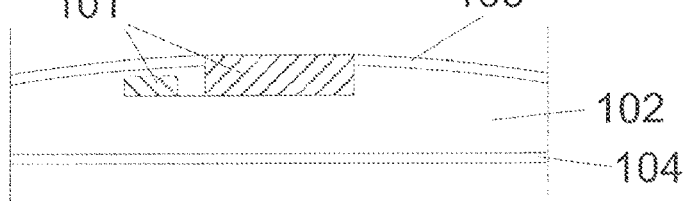
Fig.7

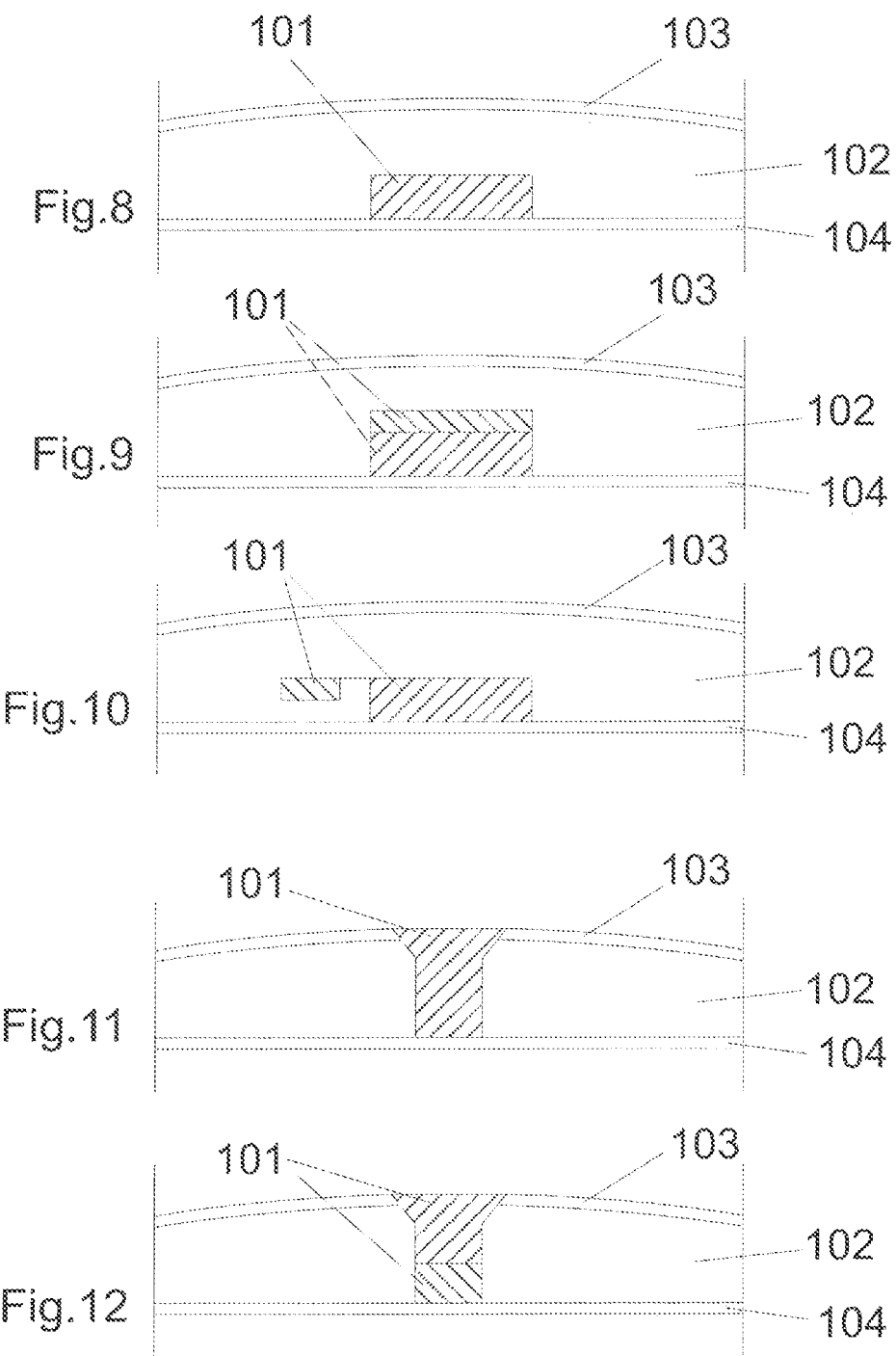

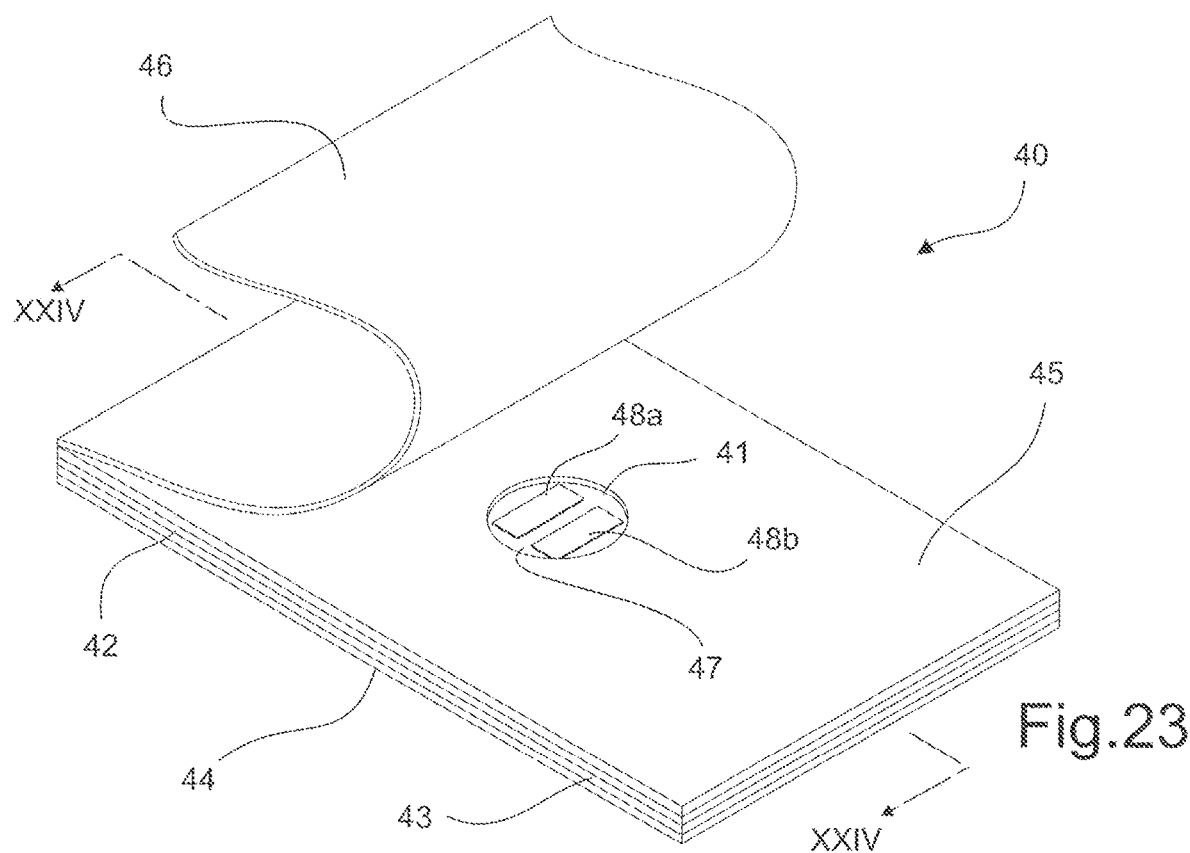
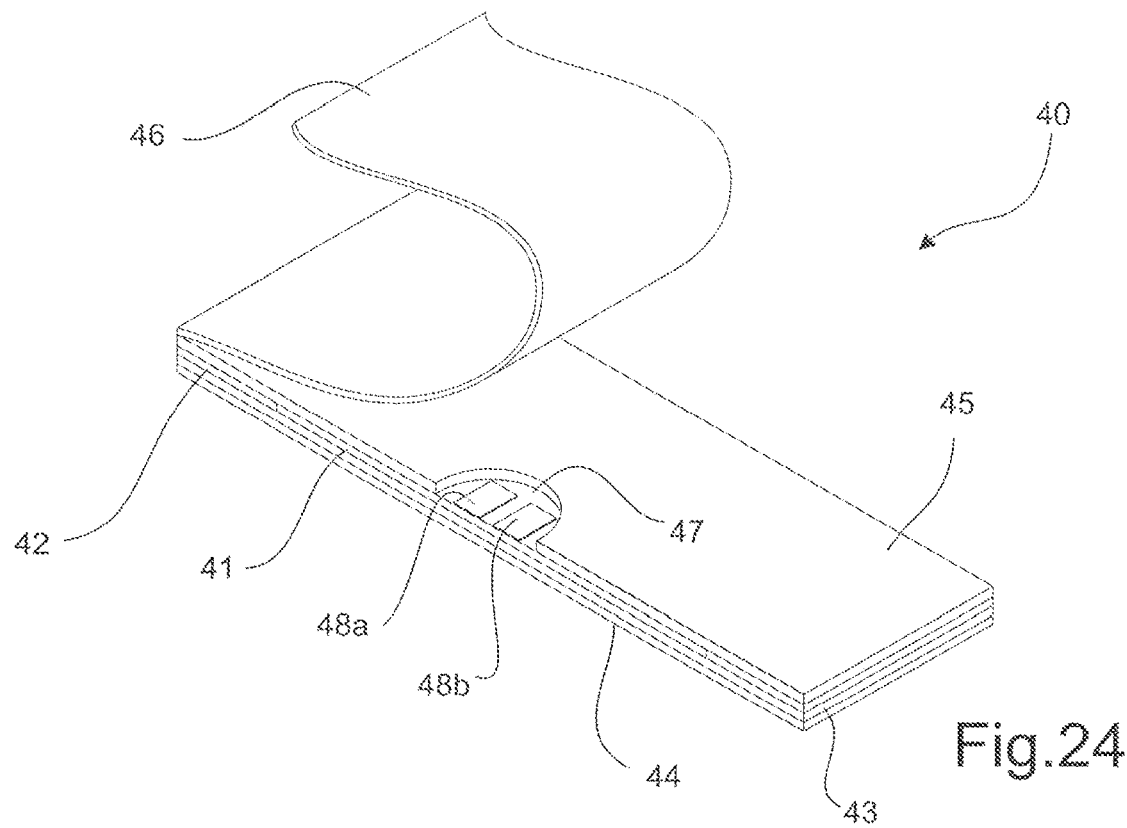

THREE-DIMENSIONAL ADHESIVE DEVICE HAVING A MICROELECTRONIC SYSTEM EMBEDDED THEREIN

This application is a continuation application of copending application Ser. No. 11/886,032, filed Apr. 3, 2008, which was a national stage of PCT/DK06/050006 filed Mar. 9, 2006 and published in English, which claims priority to DK PA 2005 00354, filed Mar. 9, 2005 and DK PA 2005 01748, filed Dec. 9, 2005, the entire contents of each of which are hereby incorporated by reference.

FIELD OF INVENTION

The invention relates to micro electronic systems predominantly for monitoring physiological or neurological conditions. More particular the invention relates to invasive and non-invasive microelectronic systems embedded in a three-dimensional adhesive device, which may be attached to the surface, suitably the skin, of a mammal. The microelectronic systems suitably utilises wireless communication and are useful for measuring ECG (Electro CardioGraphy), Etv1G (Electro MyoGraphy), EEG (Electro EncephaloGraphy), blood glucose, pulse, blood pressure, pH, and oxygen.

BACKGROUND

The attachment of sensing systems to the skin by means of pressure sensitive adhesives is well established. Thus, AMBU A/S, DK has a number of products for measuring ECG, which is attached to the skin by foam adhesives, micro-porous adhesives or hydrogel adhesives. These sensors are in general connected with wires to a monitoring device.

In WO 03/065926 A2 Ozgus et al disclose a wearable biomonitor with a flexible and thin integrated circuit. The patent application addresses a way to achieve high comfort of wear by using a thin layer adhesive or pads of adhesive for fixation to the skin. However, the adhesives used are occluding. The application further describes a sensor module for wireless data collection having a thin sheet of silicon comprising the circuit and a flexible power source being build into the sensor module as layers.

In U.S. Pat. No. 5,054,488 Mus et al disclose an optoelectronic sensor for producing electrical signals representative of a physiological condition. The sensors may be attached to the body by a double-sided pressure sensitive adhesive on a polyester lining.

In U.S. Pat. No. 5,458,124 Stanko et al disclose electrocardiographic-electrodes being attached to the body by double-sided pressure sensitive adhesive.

In U.S. Pat. No. 6,372,951 Ter-Ovanesyan et al disclose a sensor operatively connected to a disposable article, fitted to the wearer by an adhesive patch. A wide variety of body adhering compositions may be used.

In U.S. Pat. No. 6,385,473 Haines et al disclose a laminated sensor device attached to mammalian subject with two strips of hydrocolloid adhesive. The laminated structure consists also of hydrogel in contact with hydrocolloid adhesive. The lifetime of the device is specified to 24 hrs.

In WO 99/59465 Feierbach et al disclose an apparatus for monitoring the physiological condition of a patient. The apparatus includes a patch having a distal side for being fixed to the patient. Also the apparatus may include an electronics housing that may be coupled with said patch. In one embodiment the surface of the apparatus may be preformed to the contours of a body part. The patch carrying the electronic housing may be soft and provide a natural feel and may be produced from latex, silicon or another rubberised fabric. The upper surface of the patch with the electronic housing may have a smooth convex shape as illustrated in FIG. 2B and FIG. 8 of the patent. The patch is coupled to the skin of the patient by an adhesive. Such adhesive may be a hydrocolloid skin protective adhesive manufactured by 3M. Hence the patent application teaches the use of a hydrocolloid adhesive liner for fixation of a sensor having a smooth and soft backing optionally in a pre-formed shape to fit a contour of the body.

In US application 2003/0009097 A1 Sheraton et al disclose a sensor having a hydrogel electric conducting central skin contacting part and a hydrocolloid adhesive part surrounding this central part for adhesion of the sensor and on said combined disc a conductive terminal connected to a wire. This construct is further protected by laminate film layers adhered to the terminal and the outer rim of adhesive. The patent application teaches the use of hydrocolloid adhesives for fixation of sensors to the skin and emphasizes the aspect of making very thin and flexible electrodes. The patent application is peculiar in the sense that it combines the use of hydrocolloid adhesives and hydrogels. For any practical purpose the disclosed constructs will be useless as the moisture from the hydrogel will migrate into the hydrocolloid adhesive and disrupt this over time.

Recent developments in devices for monitoring physiological conditions are wire-less types. Apart from being able to monitor a physiological condition invasively or non-invasively and potentially compare to a reference, they are be able to process data and transmit them to a portable device. In fact the attachable device may also function as an alarm itself, e.g. by use of e.g. light emission, audio alarm or another warning signal.

When monitoring physiological or neurological conditions of the human body it is important that the attached microelectronic system is as comfortable to wear as possible, especially when the person carrying the device is not bedridden and shows normal physical activity or even excess physical activity like in sport or in sports medicine. The user should preferably not feel the attached microelectronic system and the monitoring should preferably be kept in private. However, in this respect the known microelectronic systems suffer from several major drawbacks as described below.

Attachment to the skin by means of occlusive pressure sensitive adhesives often leads to skin irritation due to the occlusion of moisture and due to irritants, such as monomers from the pressure sensitive adhesive polymer system, e.g. from for instance acrylic adhesives. Irritation may be the in form of itching and erythema and may especially develop when the adhesive device is attached for a prolonged period of time. Occlusion may also increase the risk of creating allergy to the adhesive composition. One often used way to solve the negative effects of occlusion is to use micro porous tapes, but such tapes are essentially two-dimensional and thin and does not protect the microelectronic system from shear forces due to friction against clothes and the like.

In the above references, the devices are attached to the skin by thin planar adhesive layers carrying the microelectronic system as a bulky part leading to discomfort of the patient or person carrying the device due to stiffness or friction against clothing and increasing the risk of involuntarily detachment from the skin. When such a device is to be used for a prolonged period of time, it is important to reduce any type of discomfort due to skin irritation or inconvenience of carrying a bulky device. Furthermore it is crucial for the signal detection that the adhesive device is kept fixed to the skin until it is deliberately removed.

Proper adhesion of the device requires a fairly thick layer of the planar adhesive. However, a fairly thick layer may show a tendency of adhering at the edge to clothing or linen and by doing so a tendency to roll and detach is created.

Many sensors are connected to the monitoring systems with wires. The disadvantage of such a system is that the patient does not have freedom to move since the wires are attached to the sensors on the body and connected to a monitoring system. Whenever the patient wants to move he must be careful not to dislodge any of the wires attached to the sensors, and he must further pick up the monitoring system and carry it along.

None of the above mentioned references describes a body sensor device consisting of an optionally hydrocolloid containing thermoplastic pressure sensitive adhesive and/or chemically curing pressure sensitive adhesive, moulded or cast into a three-dimensional adhesive body having a micro electronic system embedded therein as according to the present invention.

The known sensors overcoming some of the above-mentioned disadvantages are not as simple and inexpensive to manufacture with respect to the adhesive part of the device as the adhesive devices of the invention.

The adhesive devices of the invention having a microelectronic system embedded therein may be produced relatively easily and besides a cover layer and optionally a release layer, without the need of any other layers in the device and is therefore commercially attractive.

With an embedment of the micro electronic components an improved protection against mechanical damage and penetration of moisture from the surrounding environment is also achieved.

Furthermore, today many types of electronics are temporarily attached to different surfaces. Especially within medical care different types of medical devices such as probes and sensors are attached to different areas of the skin in order to, for example, detect different biomedical signals or retrieve samples from a patient. Often these medical devices are only attached for a limited period of time until a disease is diagnosed or a patient's health has improved. However, some chronic diseases may require periodical monitoring, for example while the patient is sleeping, or in some eases constant monitoring is desired day and night. The medical device, which is attached to the skin of the patient, may be adapted to detect many types of signals, it could for example be a sensor for detecting one or more signals such as electromyographic (EMO) signals, electrocardiographic (ECG) signals and electroencephalography (EEG) signals.

Such medical devices may be broken up into at least three general elements, a microelectronic element for measuring a desired value, such as for example a biosignal; an adhesive for attaching the microelectronic element to a surface; and a power source for powering at least a part of the microelectronic circuit.

The different elements have different lifespan, however, since the elements are typically assembled in one inseparable unit they are all disposed after use. When looking at the elements individually it may however be understood that they have different lifespan. Thus, the adhesive element typically has a one-time use only. The power source may in some eases be reused a few times depending on the application and the size of the battery. However, the microelectronic element may be reused a large number of times thereby making it an expensive element to dispose after one use only.

Thus in order to improve the cost effectiveness of the medical device there exists a need to be able to reuse the element(s), which are still operable after use.

US 2002/0180605 discloses a method of monitoring a physiological characteristic. The method disclosed can include subsequent steps of removing adhesive pads from a sensor module and heating the senor module in an autoclave for sterilization after data has been transferred from the sensor module to the receiver module.

SUMMARY OF THE INVENTION

Accordingly, the present invention relates to a three-dimensional adhesive device comprising an microelectronic sensing system characterized by (a) a three-dimensional adhesive body made of a pressure sensitive adhesive having an upper surface and a bottom surface;

(b) a microelectronic system embedded in the body of the pressure sensitive adhesive;

(c) one or more cover layer(s) attached to the upper surface; and (d) optionally a release liner releasable attached to the bottom surface of the adhesive device, Suitably, the microelectronic system is a microelectronic sensing system. The microelectronic sensing system is suitably capable of sensing physical input such as pressure, vibration, sound, electrical activity (e.g. from muscle activity), tension, blood-flow, moisture, temperature, enzyme activity, bacteria, pH, blood sugar, conductivity, resistance, capacitance, inductance or other chemical, biochemical, biological, mechanical or electrical input.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 1 shows a die section of the shape of a typical representative of the adhesive device according to the invention. CT is the maximal thickness of the device and PT is the thickness in the periphery of the device.

FIG. 2 illustrates a microelectronic system embedded/integrated in a three-dimensional (3D) adhesive. The zoom-box indicates the part of the adhesive device illustrated in FIGS. 3, 4, 5, 6, 7, 8, 9, 10, 11 and 12.

FIG. 3 illustrates a microelectronic system (hatched box) that is completely integrated within the adhesive body.

FIG. 4 illustrates that parts of the microelectronic system may be positioned in different locations integrated within the adhesive device with proper mechanical or electrical interconnection between the parts.

FIG. 5 illustrates a microelectronic system, which is applied into a recess in the adhesive body. The recess is distal to skin fixation area. The microelectronic system may optionally be exchangeable, or reusable.

FIG. 6 illustrates the microelectronic system in which the upper part may be exchangeable or reusable and the lower part be permanently integrated in the adhesive body.

FIG. 7 illustrates that parts of the microelectronic system may be situated in different locations within the adhesive device with proper mechanical or electrical interconnection between the parts.

FIG. 8 illustrates a microelectronic system, which is embedded/applied into a recess on the adhesive side of the adhesive body.

FIG. 9 illustrates a device with a microelectronic system in which the lower part may be exchangeable or reusable and the upper part be permanently integrated in the adhesive body.

FIG. 10 illustrates a system with some microelectronic components integrated within the adhesive body during production (small hatched box) and some microelectronic components applied later thereby establishing the necessary mechanical/electrical connections.

FIG. 11 illustrates a microelectronic system embedded in the adhesive which system is applicable and accessible both from the distal side and the skin fixation side of the adhesive body.

FIG. 12 illustrates a system where the microelectronic system is assembled from two parts one of which, or each of which may be exchangeable or reusable.

In all the above constructs of the invention the upper surface remains smooth irrespective the presence of components of the microelectronic system at the upper surface. This may be achieved by proper construction of the microelectronic components, encapsulation etc.

The constructions shown in FIGS. 8, 9, 10, 11 and 12 are particularly suitable for microelectronic systems including an element, e.g., an electrode which should have skin contact.

Figure 14:
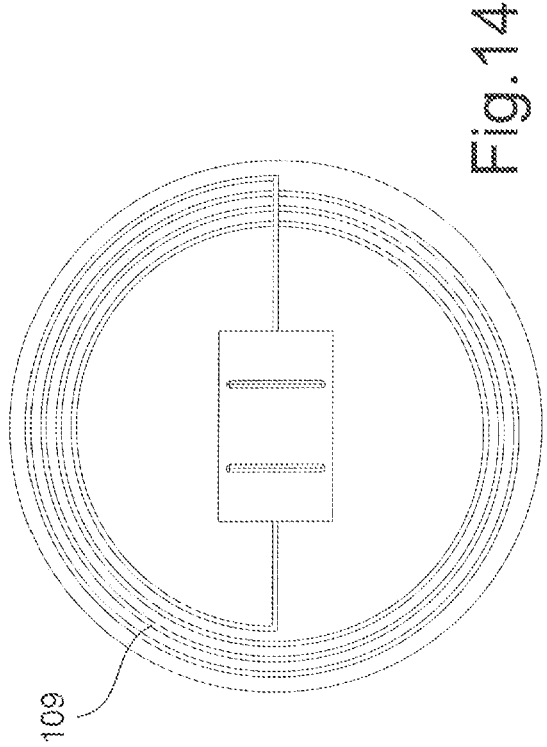
Figure 16:
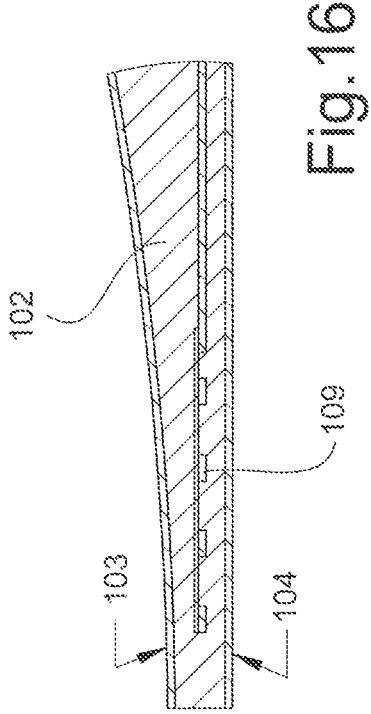
Figure 13:
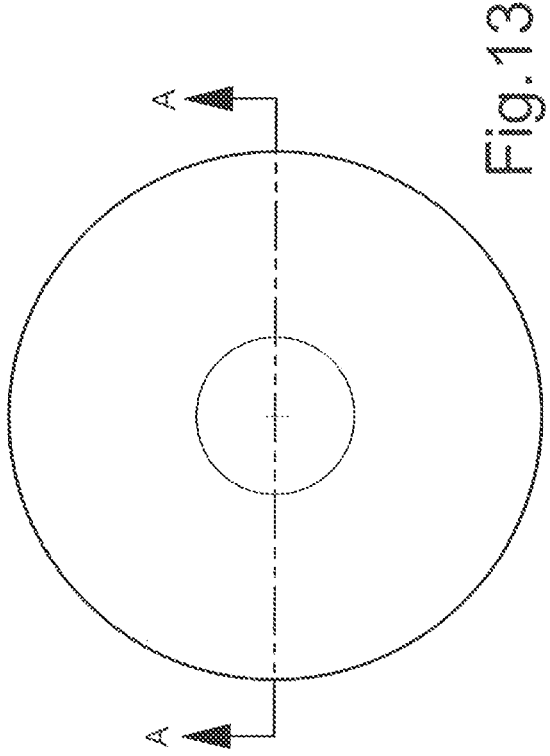
Figure 15:
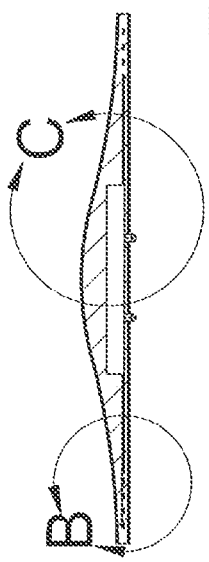
Figure 17:
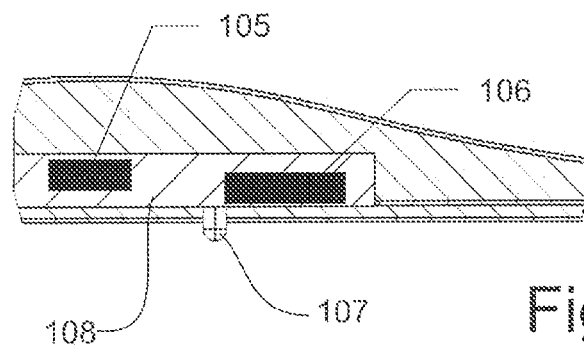
Figure 18:
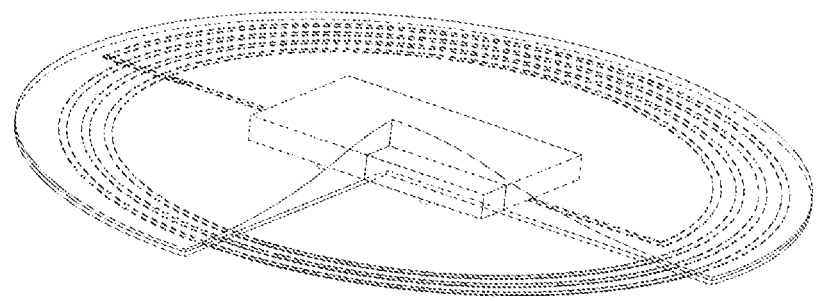

FIGS. 13-18 illustrates an embodiment of the invention where an antenna, a Central Processing Unit, a battery and electrodes are embedded in an adhesive device. FIG. 13 illustrates the two-dimensional shape of the device indicating a cross-section by A-A. In FIG. 15 the third dimension is shown as the cross-section A-A. The circle B from the rim of the device is further magnified in FIG. 16 and the circle C of the centre is like wise magnified in FIG. 17. FIG. 14 illustrates the position of the antenna placed in the outer part of the adhesive device and being connected to the central part of the microelectronic system. FIG. 16 shows more in detail the building of the antenna lying embedded in the adhesive. FIG. 17 shows the position of the central part of the microelectronic system with a battery, a CPU and an electrode protruding the adhesive. The battery and the CPU are enveloped in a transparent silicone rubber. Finally FIG. 18 illustrates the adhesive device in a three-dimensional mode, FIG. 19 shows one embodiment of a sensor assembly according to the invention seen in a exploded perspective view.

Figure 19:
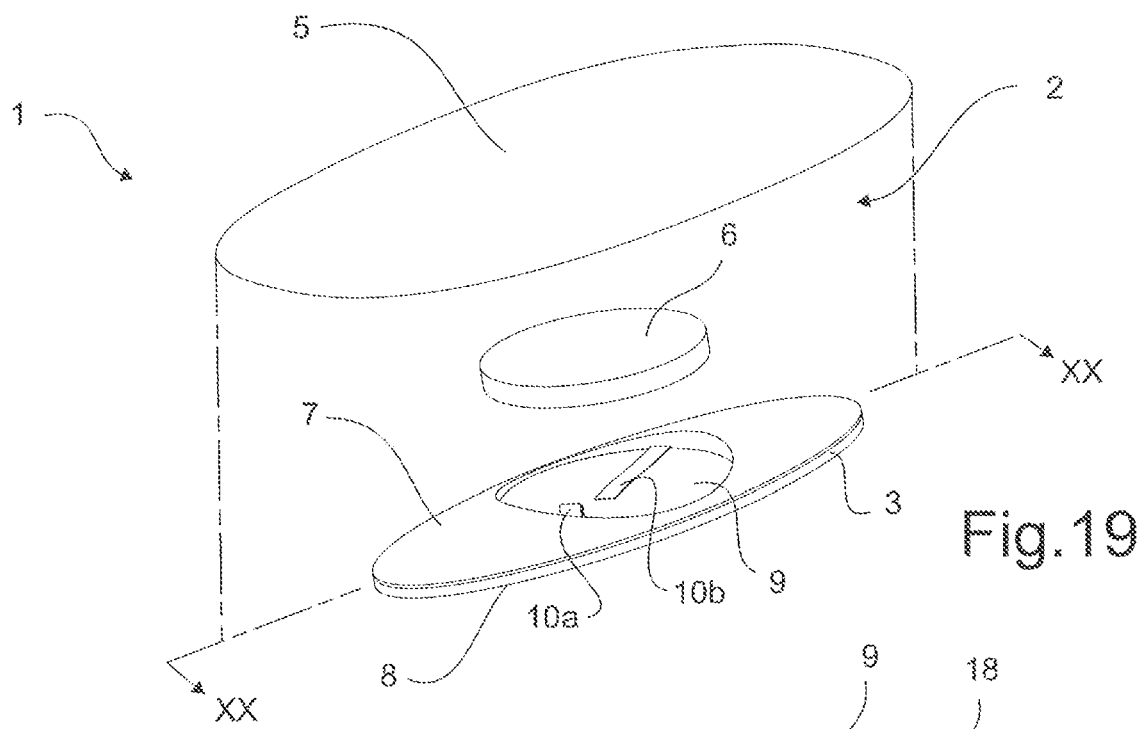
Figure 20:
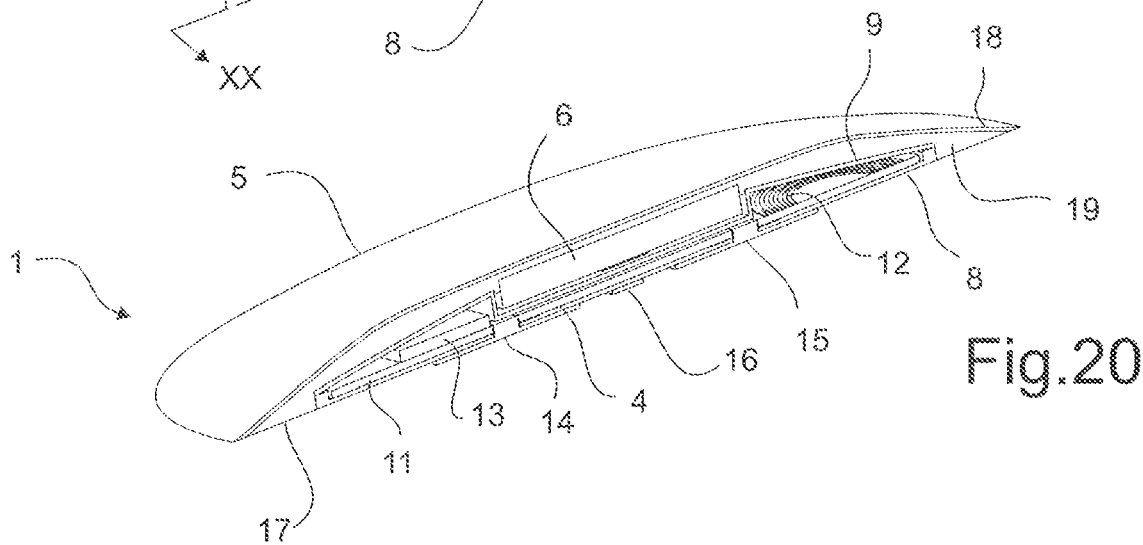

FIG. 20 shows the embodiment of a sensor assembly in a sectional view along line XX-XX in FIG. 19.

Figure 21:
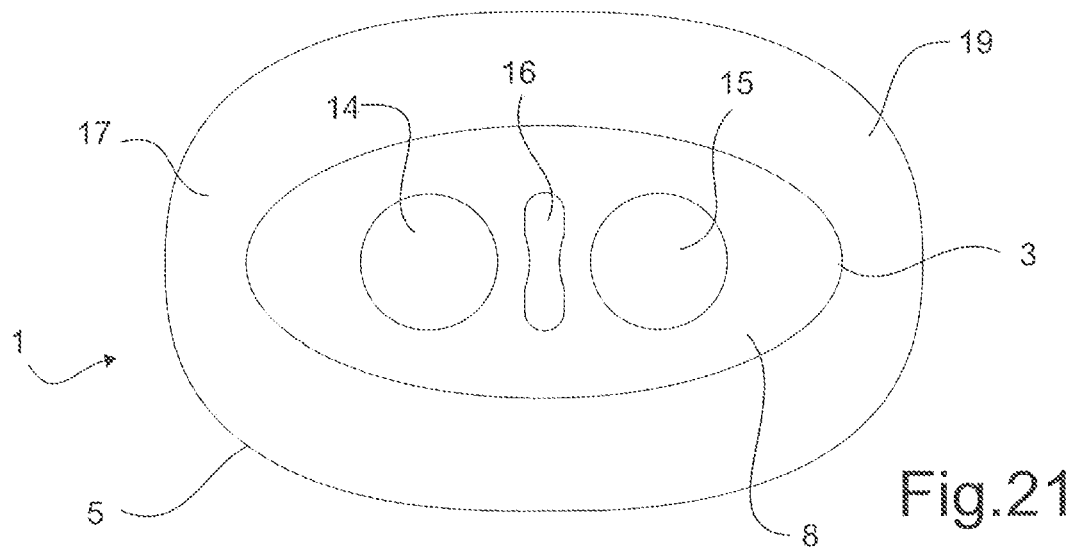

FIG. 21 shows the embodiment of a sensor assembly seen from the bottom.

Figure 22A:
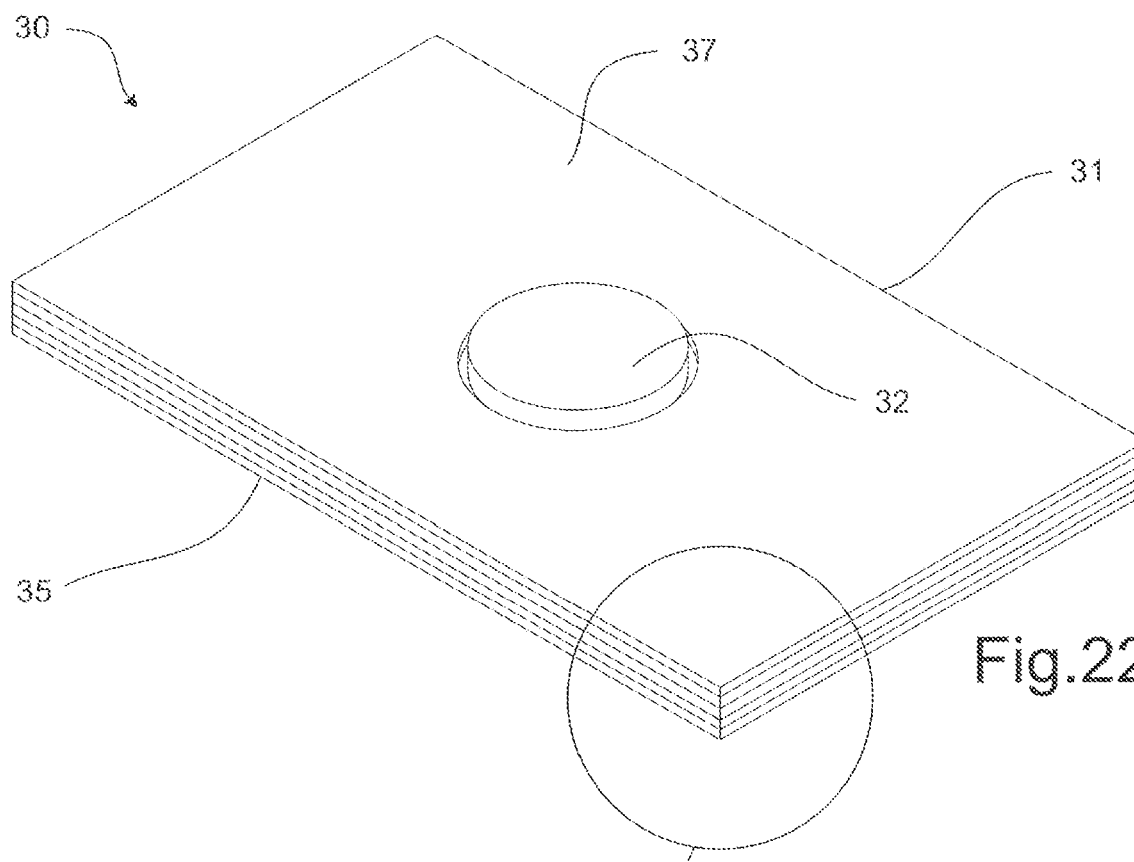
Figure 22B:
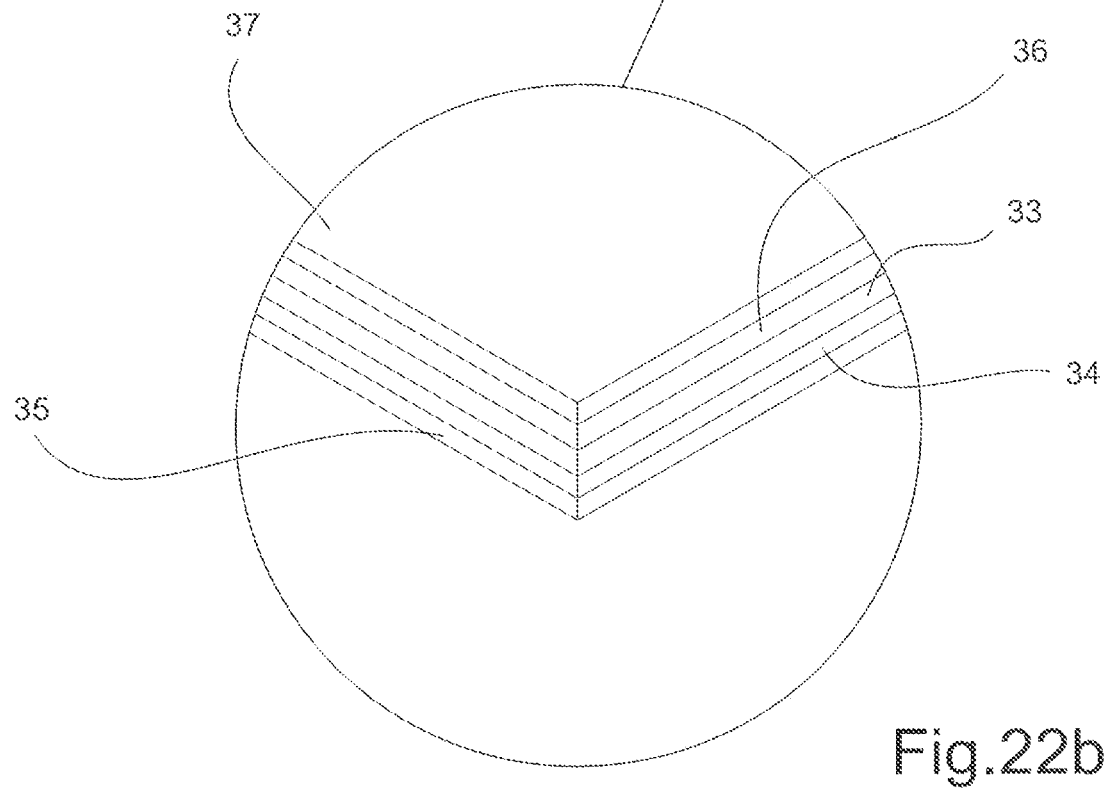

FIG. 22a and 22b shows another embodiment of a device according to the invention wherein FIG. 22b shows a portion of FIG. 22a in an enlarged view.

FIG. 23 shows yet another embodiment of a device according to the invention seen in a perspective view.

FIG. 24 shows the embodiment of a device according to the invention in a sectional view along line XXIV-XXIV in FIG. 23.

DETAILED DESCRIPTION OF THE INVENTION

Further scope of applicability of the present invention will become apparent from the detailed description given hereinafter. However, it should be understood that the detailed description and specific examples. While indicating preferred embodiments of the invention, are given by way of illustration only, since various changes and modifications within the spirit and scope of the invention will become apparent to those skilled in the art from this detailed description.

The present invention relates to adhesive devices having a microelectronic system embedded in an adhesive body made from a pressure sensitive adhesive.

In the following the term "three-dimensional" used when defining an element e.g. an adhesive body or device, refers to an element having a considerable varying contour when seen in cross section. Thus, for example a three-dimensional adhesive body will have a maximum thickness and a minimal thickness. According to the invention the maximum thickness will be at least twice the thickness of the minimal thickness. In a preferred embodiment the outer rim or the peripheral edge of the adhesive device has a thickness which is less than half of the thickest part of the sensor, normally the central part.

In contrast to the term "three-dimensional" the term "two-dimensional" used when defining an element refers to an element, which has a generally planar surface. Thus, the maximum thickness of a two-dimensional adhesive body is below two times the minimal thickness of the adhesive body.

As used herein in relation to the micro electronic system or components thereof, the term "embedded", means that the pressure sensitive adhesive of the adhesive body is surrounding all or some of components of the micro electronic system, either partly or fully. Thus, the term embedded covers the situation where all sides of the system or component(s) is covered by the adhesive of the adhesive body and also the cases where not all sides of the embedded item is covered with the adhesive of the adhesive body, e.g. when the item is placed in a recess or cavity in the adhesive body and is accessible from the outside.

As "embedded" is the general term used for the description of the way the micro electronic system is positioned in the adhesive body the term "integrated" means that the micro electronic system or specific components thereof are covered by adhesive on all sides and the term "applied" is used when the micro electronic system only is partly covered.

Integrated and covered on all sides also covers the situation where the integrated component is connected, e.g. electrically or otherwise to another component embedded in the adhesive body.

As used herein, a microelectronic "sensing" system means a microelectronic system comprising a transducer having an element capable of detecting a physiological or neurological condition.

As used herein through hole means a hole through the adhesive body having opening(s) at the upper surface of the adhesive body and opening(s) at the bottom surface of the adhesive body. Preferably the through hole has one opening at the upper surface and one at the bottom surface of the adhesive body. The through hole may have any suitable shape.

By the "thickness" of the adhesive device is meant the length of the shortest line which may be drawn between a specific point on the upper surface to a point on the bottom surface, or the shortest line which may be drawn between a specific point on the bottom surface to a point on the upper surface.

For the purpose of the present invention the expression "skin" is used to designate the outer surface of mammals.

As mentioned above, it has surprisingly been found that a re-less microelectronic systems in which the micro electronic parts are embedded in a three-dimensionally shaped pressure sensitive adhesive body solve the problems of the known sensor devices.

Due to the properties of the three-dimensional pressure sensitive adhesives, an optimal protection of the micro electronic system is created. The adhesive provide sealing towards the skin surface and the adhesive device is protected from exterior liquids due to the polymeric cover layer(s) on top of the adhesive device. Furthermore the adhesive protects the embedded micro electronic parts from mechanical damage.

The adhesive bodies according to the invention are made from pressure sensitive adhesives that arc shaped three-dimensionally, having a varying thickness from the centre to the peripheral edge of the adhesive body and having the micro electronic sensing system embedded within the adhesive body, suitably where the adhesive body is thickest.

A device with such a shape and suitably with bevelled edges provides a smooth interface with the skin. The adhesive device will give a gentle feel and will not tend to give friction to clothes and linen. A special advantage will be that the adhesive device will less easily involuntarily fall off due to bulkiness and adhesiveness at the edge. This is very important to the very function of the device.

Moreover, the construction of the adhesive device is simple and convenient as the adhesive body have a triple function as the means for fixation of the device to the skin, the means for protection of the microelectronic system and the means for shaping the device into a convenient shape. The construction require less components and process steps in the assembly of the three-dimensional device and is therefore less expensive and easier to manufacture.

According to one embodiment of the invention, the three-dimensional adhesive body has an essentially planar bottom surface adapted to adhere to the body surface of a mammal and an smooth upper surface. The adhesive device is suitably thickest at the central part of the body and thinnest at the periphery of the body. Preferably, the upper surface has a smooth convex surface, but it may in principle take any form.

The outer rim or the peripheral edge of the adhesive device must be shaped to a thickness less than half of the thickest part of the sensor, normally the central part.

Thus, in a further embodiment of the invention, the thickness of the adhesive device at the periphery is less than 50 of the thickness of the adhesive device where it is thickest, suitably the thickness at the periphery is less than 25% of the thickness of the adhesive device where it is thickest, preferred the thickness at the periphery is less than 10% of the thickness of the adhesive device where it is thickest, and most preferred the thickness at the periphery is less than 5% of the thickness of the adhesive device where it is thickest.

The thickness at the periphery of the adhesive device is typically under 0.4 mm. In one embodiment the thickness may be between 0.01 and 0.4 mm. Suitably, the thickness at the periphery of the adhesive device is above 0.05 mm, preferably between 0.05-0.4 mm.

Typically the adhesive device is between 0.5 and 15 mm, more suitably between 1-5 mm where it is thickest, typically but not necessarily, at the centre of the adhesive body.

Suitably, the angle between the bottom surface of the adhesive device and a line drawn from any point of the circumference of the bottom surface and the point at the upper surface where the adhesive body is thickest is below 60 degrees, preferably below 45 degrees and most preferably below 30 degrees.

The outer rim of the adhesive body may suitably be shaped circular or oval, with or without flaps and lobes, or it may be shaped rectangular or triangular to obtain as convenient and safe a device as possible.

Normally the outer rim of the adhesive body will consist of the adhesive of the adhesive body. However, there may be embodiments where the microelectronic system or component(s) thereof, is placed in/or at the outer rim, whereby the outer rim does not solely consists of the adhesive of the adhesive body.

The pressure sensitive adhesive making up the three-dimensional adhesive body is suitably a mouldable thermoplastic or chemically curing pressure sensitive adhesive having a flexibility enabling the adhesive device to conform to the curvature of body parts while retaining its adhesive properties even under movements.

Suitable, pressure sensitive adhesives making up the adhesive body is an adhesive based on polymers selected from block-copolymers such as styrene-block-copolymers, and hydrogenated styrene-block-copolymers, amorphous poly-alpha-olefins (APAO), polyacrylics, polyvinylethers, polyurethanes, polyelhylenevinylacetate, silicone or from the group of hydrogel pressure sensitive adhesives.

Pressure sensitive adhesives based on these polymers are known and the skilled person knows how to prepare adhesives based on these polymers.

The block-copolymers, such as styrene-block-copolymers, and hydrogenated styrene-block-copolymers, may suitable be selected from Styrenelethylene-Butylene/Styrene (SEM), Styrene/Isoprene/Styrene (SIS), and Styrene/Ethylene-Propylene/Styrene (SEPS).

The adhesive may also be based on PDMS (polydimethylsiloxane), and may suitably be a PDMS gel.

Hydrogel adhesives may also be based on or comprise amfifilic polymers, polyvinylpyrrolidone, polyvinyl alcohol, polyethyleneoxide, gelatins, natural gums and cellulose derivatives or any combinations thereof.

The pressure sensitive adhesive may be formulated according to the principles and based on the polymers listed and disclosed in the handbook of Donatas Satas; Handbook of pressure sensitive adhesive technology, Third edition.

In one particular embodiment of the invention, the pressure sensitive adhesive making up the adhesive body comprises hydrocolloids. The pressure sensitive adhesive comprising the hydrocolloids may be any of the above-mentioned types of pressure sensitive adhesive or any other pressure sensitive adhesive known in the art.

Thus, U.S. Pat. No. 3,339,549 discloses a blend of a rubbery elastomer such as polyisobutylene and one or more water-soluble or water swellable hydrocolloids such as a powdery mixture of pectin, gelatine and carboxymethylcellulose. The adhesive mass has a water-insoluble film applied to one surface. A composition of this type is available commercially from E.R. Squibb & Sons Inc. under the trademark "Stomahesive" and is used as a skin barrier around stomas to prevent skin breakdown by the corrosive fluids discharged by the stoma.

In adhesive compositions of this type, the polyisobutylene is responsible for provision of the adhesive properties and the dispersed hydrocolloid powders absorb fluid and render the adhesive agent capable of also adhering to moist skin (wet tack). These compositions are also gaining increasing acceptance as wound dressings for dermal ulcers, burns and other exuding wounds.

In a number of embodiments, styrene copolymers have been incorporated which are disclosed in a number of patent references. Thus, U.S. Pat. No. 4,231,369 Sorensen et al. disclose an ostomy skin barrier consisting of a styrene copolymer having dispersed therein a water-soluble hydrocolloid gum and a tackifier.

In U.S. Pat. No. 4,367,732 Poulsen et al., disclose an ostomy skin barrier consisting of a water soluble hydrocolloid dispersed in a continuous phase consisting of a styrene copolymer, a hydrocarbon tackifier, and a plasticizer, an antioxidant, and an oily extender.

U.S. Pat. No. 4,551,490 (Doyle et al.) discloses medical grade pressure sensitive adhesive compositions comprising a homogeneous mixture of 5-30% of one or more polyisobutylenes, 3-2.0% of one or more styrene radial or block type copolymers having a content of diblock copolymer below 20%, mineral oil, one or more water soluble hydrocolloid gums, and a tackifier. One or more water swellable cohesive strengthening agents, an antioxidant, and various other optional ingredients also may be included within the adhesive composition.

U.S. Pat. No. 5,492,943 discloses a pressure sensitive adhesive composition including a blend of two viscoelastic adhesive elastomers, specifically, high molecular weight polyisobutylene and a styrene block copolymer, which along with a plasticizer (preferably petrolatum) and a suitable tackifier and antioxidant, form a continuous phase in which hydrocolloids such as sodium carboxymethylcellulose and pectin are dispersed.

In U.S. Pat. No. 4,867,748 Samuelsen disclose geometries of sealing pads from hydrocolloid adhesives combined with backing films and the processing of such.

The adhesive compositions disclosed in U.S. Pat. No. 5,492,943 are stated to be used for wafers for adhering ostomy appliances to the skin and differ from known compositions by comprising styrene block-copolymers having a higher content of diblock copolymer, completely avoiding the use of low molecular weight polyisobutylene and furthermore by preferably not including gelatine.

Pressure sensitive adhesives containing hydrocolloids is a particularly suitable group of adhesives being characterized by having a particulate phase of hydrocolloids dispersed in the adhesive phase. An adhesive containing hydrocolloids may absorb moisture from the skin avoid occlusion of the skin, while maintaining its adhesive properties to skin. Moreover, and adhesive body containing hydrocolloids may have any thickness and still having the non-occlusive properties. A hydrocolloid adhesive may be processed as a hot melt and is easily moulded into specific shapes.

This means that the hot melt property combined with the easy moulding enables graduation of the thickness of the adhesive body from the edge of the adhesive device comprising the microelectronic system to the central parts giving a smooth non-abrupt projecting profile. Recipes for making pressure sensitive adhesives useful for an adhesive body according to the invention are described in more detail below.

Thus, a typical pressure sensitive adhesive composition comprises a substantially homogeneous mixture of 10-60 weight percent of one or more rubbery elastomeric components, 5-60% of one or more absorbent particles, 0-50% tackifier resin, 0-10% of a plasticiser and 0-60% of a non-polar oily extender, based on the total weight of the composition.

The rubbery elastomeric base could be selected from the group consisting of physically cross-linked elastomers (suitably block copolymers containing polystyrene blocks), a chemically cross-linked natural or synthetic rubbery elastomer, or a rubbery homopolymer.

A physically cross-linked elastomer selected from block-copolymers of styrene, and one or more butadienes may be a styrene-butadiene-styrene block copolymer, a styrene-isoprene copolymer and is preferably a mixture of styrene-isoprene-styrene and styrene-isoprene block copolymers.

A chemically cross-linked rubbery elastomer may be e.g. butyl rubber or natural rubber.

A rubbery homopolymer may be a polymer of a lower alkene such as low density polyethylene or propylene, preferably atactic polypropylene (APP) or polyisobutylene.

A tackifying resin optionally used in accordance with the invention is preferably a hydrogenated tackifier resin and is more preferred selected from a group comprising polymers and copolymers of cyclopentadiene, dicyclopentadiene, alpha-pinene or beta-pinene.

When the physically cross-linked elastomer is a styrene-butadiene-styrene block copolymer or a styrene-isoprene-styrene block copolymer, the adhesive suitably comprise 0-10% of a plasticiser e.g. (citrofol BII, DOA).

The swelling hydrocolloid particles preferably consist of one or more water-soluble or water swelling hydrocolloid polymers or gums.

Suitable hydrocolloids include synthetic polymers that may be either linear or cross-linked, such as hydrocolloids prepared from lactams or polyvinyl pyrrolidone. Other monomers useful to prepare a synthetic hydrocolloid include acrylates, methacrylates and watersoluble amides.

Other hydrocolloidal polymers, either naturally occurring or synthetically prepared, are useful according to the present invention. These materials include polyvinyl alcohol, polyoxyalkylenes, and naturally occurring or synthetically modified hydrocolloids such as polysaccharides, gums, and modified celluloses.

Representative polysaccharides include starch, glycogen, hemicelluloses, pentosans, celluloses, pectin, chitosan, and chitin. Representative gums include Arabic, Locust Bean, Guar, Agar, Carrageenan, Xanthan, Karaya, Alginates, Tragacanth, Ghatti, and Furcelleran gums. Representative modified celluloses include methyl cellulose, hydroxypropyl methyl cellulose, carboxymethyl, cellulose, and hydroxypropyl cellulose.

Preferred hydrocolloids include polysaccharides, such as starch, glycogen, hemicelluloses, pentosans, gelatin, celluloses, modified celluloses, pectin, chitosan, and chitin. Modified celluloses include methyl cellulose, hydroxypropyl methyl cellulose, carboxymethylcellulose, and hydroxypropyl cellulose. A most preferred hydrocolloid is a water soluble or swelling hydrocolloid chosen from the group consisting of polyvinyl alcohols, powdered pectin, gelatin, methyl cellulose, hydroxypropyl methyl cellulose, carboxymethyl cellulose, hydroxypropyl cellulose and mixtures thereof. In one preferred embodiment, the hydrocolloid is carboxymethyl cellulose (CMC).

Suitable swelling colloids are small spherical particles based on cross-linked polyacrylic acid polymers. Examples of such materials may be found in U.S. Pat. No. 4,867,748, EP 0 122 344, and US patent application No. 2004065232.

Sometimes the skin for attachment of the adhesive device may be moist or even wet. In these circumstances, the normal adhesives may not give a sufficient strong and permanent attachment of the adhesive device. Specialised adhesives useful in these circumstances are hydrogel adhesives. Such adhesives are based on hydrophilic polymers and extenders enabling an even uptake of moisture over the complete skin-contacting surface of the adhesive. A wide range of compositions of such hydrophilic adhesives exists. Hydrophilic polyacrylates with high content of acid groups optionally being partly neutralised, is a major representative in this group of adhesives. These adhesives may be inherent adhesive or may be formulated with tackyfiers and extenders to the desired adhesive properties in dry conditions. When getting moist, the adhesiveness will increase vastly depending on the formulation as the uptake of water will transform the adhesive to a more plastic state. Alternative adhesives are based on polymers like polyvinyl pyrrolidone, polyvinyl alcohol, polyethylene oxide and the like. Amphiphilic polymers or polymers which may be chemically cross-linked by radical polymerisation may be added to improve the cohesion of the adhesive and extenders like polyethylene glycol, polypropylene glycol and glycerol are typically preferred.

Adhesive compositions based on polydimethylsiloxane (PDMS) have been known since the 1970's. Recently a new subclass of PDMS based pressure sensitive adhesives has developed namely soft silicone adhesives. Soft silicone adhesives (SSA's) are two-part, solventless adhesives based on a cross-linked, silicone elastomeric structure. The cross-linking is a result of an addition reaction between a polydimethylsiloxane with vinyl groups and hydrogen functional siloxanes. The cure reaction is catalysed by a platinum complex and can occur at room temperature or can be accelerated at elevated temperature (80 degree C. to 145 degree C.) without the formation of by-products. Such adhesives are characterised by being soft and by conforming to the surface structure of the skin, whereby quickly wetting of the skin is achieved. Because the viscous component is minimal, the material does not flow and only small dissipation of the energy occurs when deformation pressure is applied. The result is an immediate debonding, which happens at low-peel or shears force, which for some instances may be advantageous.

Apart from being excellent skin adhesives PDMS based pressure sensitive adhesives may have the further properties of being reusable, since they can be cleaned with tap water and be reapplied to the skin.

The pressure sensitive adhesive used for making the adhesive body of the invention could also be a PDMS gel often described as a tacky gel. Examples of such commercially available systems are Dow Corning 7-9800 A&B, from Dow Corning HealthCare US or SilGel 612 from Wacker-Chemie GmbH, Burghausen, Germany, and MED-6340 from NuSil Technology, Carpinteria, USA.

The above mentioned pressure sensitive adhesive can either be used in a non-foamed version or in a foamed version. When gas bubbles are introduced into pressure sensitive adhesives during the manufacturing process a lightweight, cellular structure is produced. Such a pressure sensitive adhesive is more flexible than the non-foamed versions. (see U.S. Pat. No. 6,326,524 and US patent application No. 2004065232).

In general the adhesive body of the present invention has the desirable elastic, adhesive, moisture transmitting and/or absorptive properties as well as a high conformability and flexibility. The flexibility provides a composition that has the ability to conform to the curvature of body parts while retaining its adhesive properties even under movements. The high initial tack at room temperature provides for easy application of the adhesive device.

The adhesive device of the invention has on the upper surface one or more cover layers of any nature, preferably only one cover layer, to protect against adhesion to linen, clothes and other environment.

As a cover material, it is preferred to use a film in the form of a thermoplastic polymer film or a woven or non-woven layer. The cover layer is preferably made of an elastic material. The cover layer is suitably capable of transmitting moisture and may e.g. be made from polymers such as polyolefin types e.g. polyethylene, polypropylene or polybutylene, polyamide such as nylon, polyurethane, polyvinyl acetate, polyvinyl chloride, fluorinated polyvinyl compound, polyvinylidene chloride, polyvinyl alcohol, ethylene vinyl acetate, cellulose acetate or other thermoplastic polysaccharides, polyether block amides like PEBAX, block copolymers like styrene-isoprene-styrene block copolymers or ethylene acrylate block copolymers, polyesters such as polyethylene terephthalate (PET) or derivates thereof and any laminates from such polymers. The cover layer may suitably be a thin foam layer like made from polyurethane, polyethylene or polyvinyl acetate.

The cover layer or film protects the integrated/embedded microelectronic components as well as the adhesive body against the environment.

In one particular embodiment of the invention, an antenna can be printed directly on the cover layer by means of conductive ink or printed metal.

Prior to application to the skin a protective release liner covers the skin contacting side of the pressure sensitive adhesive body, in order to ensure that the properties of the adhesive are preserved and that the adhesive surface is not laid open until just before the use. The release liner is suitably a siliconised or fluorinated release liner, such as a siliconised or fluorinated craft paper, polyethylene, polypropylene or polyethylene terephthalate film. Suitably, the release liner is a siliconised polyethylene film, such as medium density polyethylene from the company Huhtamaki.

The microelectronic system comprises a number of components, which may be assembled into one, optionally encapsulated unit, which is incorporated into the adhesive device of the invention. The components of the microelectronic sensing system may also be an assembly of the individual; optionally encapsulated, components located at different positions in the adhesive device. This embodiment of the invention covers the situation where the adhesive devices have all the individual components of the microelectronic device located in different positions, as well as the situation where one or more of the components is located at a position different from the position of the rest of the components which are located at the same position.

When the components of the microelectronic device are located at different positions in the adhesive device, the adhesive device also has the necessary mechanical or electrical connections between the components integrated into the adhesive body.

Thus, according to one embodiment of the invention, the entire microelectronic system is integrated into the adhesive body and is completely covered by the adhesive body on all sides.

According to another embodiment of the invention, the entire microelectronic system is contained in a recess provided in the upper surface of the adhesive body facing the cover layer.

According to another embodiment of the invention, the entire microelectronic system is contained in a recess provided in the adhesive bottom surface of the adhesive body.

In another embodiment of the invention, the microelectronic system is contained in a through hole in the adhesive body and is accessible from both the upper surface facing the cover layer and from the adhesive bottom surface.

In an alternative embodiment of the invention, one or more components of the microelectronic system is integrated into the adhesive body and is covered by the adhesive body on all sides and the other component(s) of the microelectronic system is located elsewhere in the adhesive body, the components of the microelectronic sensing system having the necessary mechanical and electrical connection to each other.

According to the above mentioned embodiment of the invention, one or more components of the microelectronic system may be integrated into the adhesive body and covered by the adhesive body on all sides and the rest of the microelectronic system is contained in one or more a recesses (suitably one recess) provided in the upper surface of the adhesive body facing the cover layer.

Alternatively, one or more components of the microelectronic system is integrated into the adhesive body and is covered by the adhesive body on all sides and the rest of the microelectronic system is contained in one or more recesses (suitably one recess) provided in the adhesive bottom surface of the adhesive body.

In another alternative embodiment one or more components of the microelectronic system is integrated into the adhesive body and is covered by the adhesive body and the rest of the microelectronic system is contained in one or more through holes (suitably one through hole) in the adhesive body and is accessible from both the upper surface facing the cover layer and the adhesive bottom surface.

In still another embodiment one or more components of the microelectronic system is integrated into the adhesive body and is covered by the adhesive body, while other components of the microelectronic system is contained in one or more through holes (suitably one through hole) in the adhesive body and is accessible from both the upper surface facing the cover layer and the adhesive bottom surface, and the rest of the microelectronic system is contained in one or more recesses (suitably one recess) in the upper and/or bottom surface of the adhesive body.

In still an alternative embodiment one or more components of the microelectronic system is contained in one or more through holes (suitably one through hole) in the adhesive body and is accessible from both the upper surface facing the cover layer and the adhesive bottom surface and the rest of the microelectronic system is contained in one or more recesses (suitably one recess) in the upper and/or bottom surface of the adhesive body.

In another suitable embodiment one or more components of the microelectronic system is contained in one or more recesses (suitably in one recess) in the upper surface of the adhesive body and the rest of the microelectronic system is contained in one or more recesses (suitably one recess) in the bottom surface of the adhesive body.

Where the microelectronic system or components thereof is placed in the upper surface of the adhesive body, they are suitably formed with an upper surface following the contours, or shaped to fit the upper surface of the adhesive body. This may be achieved by proper encapsulation of the components.

As mentioned above, the individual components, groups of individual components or all the components of the microelectronic system may be encapsulated before they are embedded into the adhesive body. Encapsulation is chosen when additional protection of the components from the environment and/or the reverse is desired, e.g. when already present in the adhesive body or during the production process leading to integration into the adhesive body. The encapsulated components of the microelectronic system are connected to each other via the necessary electrical and/or mechanical connections.

In some cases it is required that the micro electronic system or components thereof are protected from humidity and/or perspiration in the adhesive since this will initiate corrosion, or needs shielding from exterior influence for other reasons. In such cases the micro electronic system or components thereof is encapsulated.

A number of encapsulation techniques are known and includes coating, hot-melt encapsulation, ceramic encapsulation and glass encapsulations. Other methods for encapsulation of electric components are known in the art.

The microelectronic system or components thereof is suitably encapsulated in a polymer film, a polymer foil, or a polymer coating or the microelectronic system or components thereof is moulded into a polymer material, or is encapsulated in a glass or ceramic material.

Encapsulation by coating typically involves coating the component(s) with materials such as epoxy, PDMS (silicone), acrylate, polyurethane or UV curing resins.

Encapsulation in silicone, such as PDMS, is particularly preferred when the microelectronic components is to be placed in a through hole or a recess in the adhesive body and where it is desirable to enable easy removal or replacement of the encapsulated microelectronic component(s), as the silicone surface is easily released from the adhesive of the adhesive body. Other materials, which are easily releasable from the adhesive, may also be used for the encapsulation.

Hot-melt encapsulation typically involves incorporation of the microelectronic system or components thereof in a thermoplastic material by injection moulding. The thermoplastic material used may be selected from Styrene-block copolymers, polyurethane, ABS (acrylonitrile-butadiene-styrene copolymer), SAN (styrene-acrylonitrile copolymer), polyvinylchloride, PDMS, POM (polyoxymethylene), polystyrene, polyester, polyacrylate, polyolefines; e.g, polyethylene or polypropylene.

The components of the microelectronic system require interconnection. Each system may consist of one or more discrete components, which need to be assembled mechanically and electrically. The mechanical or electrical connection may be established by PCB (printed circuit board), snap locks, thin flexible PCB, glue etc.

In one embodiment as described above, all parts of the micro electronic sensing system is integrated in the adhesive body during production, meaning that the adhesive device with the microelectronic system has a disposable nature.

The adhesive device according to the invention may also be constructed in such a way that components of the microelectronic system may be exchanged during the lifetime of the adhesive device or may reused in a new adhesive device.

Certain components of the micro electronic system are integrated into the adhesive body during production whereas the remaining components is applied to the adhesive device of the invention afterwards, just prior to attachment on the skin, or after attachment to the skin. The components applied to the adhesive body after production of the adhesive body is typically exchangeable, or reusable.

The component, which may be exchanged, is for example the energy source, e.g. the battery.

In a particular embodiment of the invention the entire micro electronic system is exchangeable or reusable and may be applied to the adhesive device just prior to attachment or after it has been applied to the skin.

Suitably, the exchangeable component(s) or the reusable component(s) is encapsulated as described above and forms a package, which fit a recess or hole in the adhesive body.

In the case of exchangeable or reusable components they must have some sort of secure attachment to the adhesive body during use. Such attachment may be provided by an adhesive, for instance by the pressure sensitive adhesive of the adhesive body already present in the indentation, the cavity of the hole in the adhesive body.

In this case it may be preferred that the encapsulation material is a material which does not adhere too strongly to the adhesive of the adhesive body, see above.

Alternatively, the package of the encapsulated, exchangeable or reusable components is attached to the adhesive body via mechanical couplings to the adhesive body. The above-mentioned encapsulated package containing the replaceable or reusable component(s) could thus be fitted into the adhesive body by a snap lock mechanism.

The encapsulation function as a housing for the microelectronic system or components thereof and is suitably formed of from injection-moulded polymer material, but could in principle be of any material and any construction.

The package of encapsulated microelectronic component may have any suitable shape, suitably three-dimensional shape, fitting a recess or through hole in the adhesive body. On one embodiment the encapsulated electronics will have the shape of a rod shaped capsule with rounded ends.

As mentioned above, the present invention uses invasive as well as non-invasive techniques for acquiring physiological data. In the case of non-invasive measurement one or more metal electrodes may be used for the skin contact. However, any conductive material may be used for the skin contact, such as conducting polymers, conducting hydrogels and electrolytes, in case of invasive measurements regular needles or micro needles may be used. Such invasive techniques are already well known today e.g. for measuring oxygen or blood glucose.

By combining well-described components, all sorts microelectronic sensing systems may be designed and incorporated into the adhesive device of the invention. Examples of systems suited for embedment in adhesive device are systems suitable for measurement of biosensor signals, EKG, EMG, EEG, blood glucose, pulse, blood pressure, pH and oxygen.

The micro electronic system incorporated into the adhesive device of the invention typically requires the following components: Communication components, CPU (central processing unit), power source, storage components, transducer components, interconnections and optionally actuator components.

The CPU (Central Processing Unit) controls and communicates with the components of the microelectronic system. The CPU handles the execution of application software, data decisions making (like data signal processing), A/D conversion, DSP (digital signal processing), routing, timing, power management, sleep function, interruption.

The CPU is the component of the microelectronic system controlling other components and making the appropriate data analysis. In general, the more speed and data analysis required, the more power is needed. Therefore a sleep function is often used in order to save power. At certain times or if certain events happen (triggered by a very low power monitoring subsystem) the CPU wakes up, makes the necessary calculations, communicates with relevant components and return to sleep mode. Depending on need very rudimentary CPU to a full-fledged microcontroller can be used according to the invention.

The communication components control all communication to and from the microelectronic system. Suitably, the microelectronic system is a system enabling wireless communication with a receiver unit placed at a distance from the adhesive device. However, the present invention is not limited to wireless communication, such as RF-wireless communication. Other communication means could be audible or optical communication means. The component includes the necessary electronics for achieving this wireless communication but also the antenna along with the necessary hardware and software.

The antenna may be of different shape and form depending on frequency, power and signal form. Some antennas are useful for communicating information a few cm, others range several meters. Examples of antennas are; a coil around a small ferrite core (e.g. less than 4 mm in diameter, a flat coil with turns (diameter typically 10 mm or more), single and double wire radio antennas such as monopole or bipole antennas, and an antenna integrated in the adhesive.

An antenna only having few turns and a large diameter e.g, 50 mm may be laminated and integrated into the adhesive body or printed or directly on the cover layer of the adhesive device. The antenna is typically made of a metal such as copper or aluminium but could also be of conductive ink.

The power source consists of power regulating electronics, recharge electronics and an energy source, typically an internal or exchangeable battery. However other means of getting power to the microelectronic system may be suggested, such as kinetic energy conversion, fuel cells, isotope radiation, solar cells or via a radio frequency (RF) link. Further the antenna may be used for loading energy to the microelectronic system.

Preferably the power source is a battery, and may be for one time use or it may be rechargeable.

The storage component is for storage of the embedded system software and/or storage of data acquired during operation of the device. The storage component may be a part of the CPU, a component of its own or an exchangeable storage device such as FLASH RAM that can be removed and exchanged.

The transducer component is a component designed to convert energy from one form to another. The transducer is typically, but not necessarily, the sensor or sensing part of the. microelectronic sensing system. A transducer may thus be able to convert for example a physical input and the transducer will usually but not necessarily convert this energy into electrical form to be interpreted by the CPU etc.

Examples of the physical input a transducer may convert is acceleration, chemical/gas, flow, humidity, inertia, capacitance, conductance, conductivity, current, impedance, inductance, pH, resistance, resistivity, voltage, photo detection, light, magnetisme, pressure, angular, linear position, velocity, temperature, sound and mechanical force.

A tangible representative of the transducer is the detecting component. The detecting component is typically selected from electrodes (polar, bipolar), pressure sensors, needles with electrodes, accelerometers, photo detectors, microphones, ion specific field effect transistors (ISFET), a NTC (negative temperature coefficient) resistors, band gap detectors, ion membranes, enzyme reactors or condensers.

In one embodiment of the invention the transducer includes a detector for non-invasive detection, such as an electrode.

In another embodiment of the invention, the transducer includes an invasive detector, such as a needle containing an electrode.

An actuator is the reverse of a transducer. It converts energy from one form to another in much the same way as a transducer but in the reverse order. Usually it converts electric signals to physical signals. A tangible representative of an actuator is e.g. electrodes (for instance for neural- or neuro-stimulation), pumps, injection needles, light emission diodes (LED) or another light source, loudspeakers, current generators or chemical synthesizers. A possible use of actuator is at certain events decided by the CPU to activate an alarm in the microelectronic system, such as loudspeaker or LED, or to indicate low battery.

Thus, the actuator may be used as a component in the system reacting to the input obtained from the transducer component such as an alarm (visible and audible), injection pump, valve etc. It can either be a one time use, a multiple use or continuous use actuator.

Many sensing systems are only informative systems transmitting information about the physical condition of a mammal and in this case an actuator is not needed.

The microelectronic system will be modular build in the sense that in a device for a given application only some of the components may be needed. Some applications will utilize fewer components and some applications may use all components. These components can be fitted into same physical ASIC (application specific integrated circuit), electrical system or subsystem, such as but not limited to, PCBs (printed circuit boards), flexible PCBs, thick film, thin film, or ceramic technologies or the system or its components may be separately encapsulated.

RFID (Radio Frequency Identification) tags are commercially available in various sizes, ranges and functionality. When the RFID reader applies the appropriate field (e.g. an inductive field) the basic RFID tag return a bit sequence. The sequence is programmed prior to use. RFID range varies from 1 cm to app. 2 meter for passive tags (no power source included) to over 100 meters for active tags (power source included). More sophisticated RFID tags available have storage components where data can be read or stored.

The RFID tag may be incorporated into the adhesive body either as a standalone part or in combination with other microelectronic components. Complex microelectronic systems can easily be made to include various forms of RFID tags without adding significantly to the complexity or price of the system. In a complex system the tag can be used as a simple track and trace component for identification of the product, such as shelf life, life time, however it can also be utilized for identification for other systems in sensor networks.

For a stand-alone solution the RFID tag consist basically of a RF chip and a coil. Suitable forms of the RFID tag is a RFID tag encapsulated in a glass housing, a RFID tag encapsulated in plastic/epoxy (typically pill shaped), a flat RFID tag with coil and a RF chip laminated between 2 polyimide layers, or a fiat RFID tag with large coil antenna with few turns printed on or in the adhesive body and with the RF chip interconnected to the antenna without any further protection/encapsulation.

These systems can be completely integrated within the adhesive bodyduring production of the adhesive body.

The above-mentioned flat RFID tag may be sandwiched between 2 layers of pressure sensitive adhesive during production. As the RF chip is very small (1 mm×1 mm) and the coil is flexible, no rigid encapsulation is needed. The glass encapsulated RFID tag has very good chemical resistance and small size to ensure no discomfort. The RFID tag encapsulated in plastic or epoxy may be of more complex design and can be added both during and after production of the adhesive body of the invention.

The encapsulated RFID tag is a component, which may be reused, in one or more adhesive bodies. The encapsulated RFID tag is transferred from one adhesive body to another and thereby reused time after time, and is ideal for storing person specific data.

Normally embedded microelectronic systems incorporate some kind of sensor in its system, however this is not necessary for all applications.

The adhesive device of the invention may also be part of a network of adhesive sensor devices placed on different locations on the body. These individual adhesive devices may vary in complexity ranging from a small basic sensor system to more complex system, depending on location and sensing property. Some adhesive devises of the network have reduced functionality called RFD (reduced function devices) whereas other devices are FFD (Full Function Devices).

The FFD devices may function at any topology and be the coordinator of the Network, or it may be a coordinator that can talk to any other device. A RFD device is limited to star topology, it cannot become a network coordinator, it talks only to a network coordinator and has very simple implementation.

FFDs may be a dedicated network coordinator acting as communication Hub, gateway or router within the Body Area Network (BAN) and handling communication with external unit(s). A communication Hub or gateway may have large storage capacity and store data from the sensor network, and when in proximity with external unit or when otherwise appropriate wireless transmit these data.

These hubs are easily integrated within the adhesive body as no skin contact or actuator is needed, and may be placed strategically on the body. As hubs will generally be larger and more centrally placed on the body, it is of great advantage that the microelectronic hub may be completely integrated within an adhesive body as this reduces discomfort and visibility.

In case of person monitoring, the microelectronic system could incorporate GPS technology. The system is either data logging the positional data for later analysis or could transmit (e.g. via the mobile net) position. Such a system within an adhesive could be place in an inaccessible location on the body.

A GPS device incorporated in an adhesive body of the invention need not be a single device in itself, but could be an add-on to an adhesive devices comprising other microelectronic systems, so the system can transmit GPS at certain event such as alarms.

Thus, the adhesive device may also contain a micro electronic system where no physical contact between the detector and the skin of the mammal is necessary. Systems that do not necessarily use transducers with a detecting element are Network Hubs, network coordinators, gateways and GPS (Global Positioning System).

Accordingly, microelectronic systems useful for use in the adhesive device of the invention could be:

A glass encapsulated RFID tag comprising communication components and a CPU. The glass encapsulated components may suitably be embedded in the adhesive device as shown in FIG. 1.

An epoxy or plastic encapsulated RFID tag comprising communication components and a CPU. The epoxy/plastic encapsulated components could for example be embedded in the adhesive body as shown in FIG. 1 or 2.

A coil antenna and a RFID tag comprising communication components and a CPU laminated between two polyamide layers. The system may be embedded in the adhesive body as illustrated in FIG. 1A.

A coil with few turns and a non-encapsulated passive read/write RFID tag comprising storage and communication components and a CPU. The system may be embedded in the adhesive body as illustrated in FIG. 1A.

A passive read/write RFID tag comprising storage and communication component(s) and a CPU encapsulated in an epoxy or plastic pill. The system may be embedded in the adhesive body as illustrated in FIG. 2.

An active read/write RFID tag encapsulated in a epoxy/plastic pill comprising storage and communication components, a CPU and a battery. The system may be embedded in the adhesive body as illustrated in FIG. 1.

RFID tags of the above-mentioned type are commercially available.

The microelectronic system may also be a gateway comprising storage and communication components, a CPU and a battery encapsulated in plastic and working as a dedicated network coordinator for transmission of data to a central unit (CU). Such a microelectronic system may for example be embedded in the adhesive body as illustrated in FIG. 1.

The microelectronic system may also be a system comprising storage and communication components, a CPU, battery, GPS, components for wireless synchronisation of real time clock for data logging of GPS data, optionally encapsulated in plastic, or a system comprising storage and communication components, a CPU, battery, GPS, components for wireless synchronisation of real time clock for data logging of GPS data, mobile net for data logging and transmission of data and position to mobile phones, optionally encapsulated in plastic. These systems may also be embedded in an adhesive body as illustrated in FIG. 1.

The adhesive device according to the invention may also be used for applications where body implants are applied electrical power and electrical data communications via wireless means across the skin barrier (trans-cutaneously). In these cases it is important to fix the adhesive device at an exact spot on the skin surface for long periods of time with minimal annoyance or inconvenience for the person carrying the device.

A typical example of wireless trans-cutaneous power transfer and electronic data communication is in implanted nerve stimulators for people who suffer from disable control of their muscles in the lower part of their leg (the drop foot syndrome). The drop foot stimulator is implanted inside the leg and has direct contact the nerves controlling the relevant muscles. The implant is typically powered wirelessly by means of an electromagnetic coupling between a coil or an antenna inside the leg and a coil or antenna placed nearby on the outside of the body on the skin surface.

The coil or antenna is connected to the electronics providing the needed power and control signals. The timing for the simulation signal is normally controlled by a pressure sensitive switch at the heel of the person or in his shoe. Often the transmission of the signals from the switch to the simulator placed on the skin of the leg is wireless.

These drop foot simulators will be substantially improved by using the adhesive device described in the invention. It enables reliable power and data transfer because of the very stable fixation of the external part of the simulator on the skin surface for long periods of time with minimal inconvenience. Further it can also enable better long-term fixation of the switch placed on the foot.

Thus, in one embodiment, the microelectronic system is useful for nerve stimulation and comprises storage and communication components, a CPU, power source and transducer for transmitting data and power to implant for nerve stimulation. The system may suitably be embedded in the adhesive body as illustrated in FIG. 3.

In another embodiment, the embedded microelectronic system is useful for surface electromyography (sEMG) or invasive electromyography. In both cases the transducer is a relatively simple 2-3 electrode device. The signal measured is a direct voltage generated by a muscle or a muscle group. In order to understand this signal it must be analysed either by the microelectronic system or stored for future analysis.

The data collected are transmitted to a Central Unit (CU) either when relevant. When certain events occurs or at certain time intervals. The CU is suitably a portable hardware device with wireless reception/sending capability, such as but not limited to a PDA (personal digital assistant), a mobile phone or other dedicated hardware.

The transducer is suitably designed to overcome or neglect the difference from time to time of the surface resistance of the skin. Dry skin has resistance of e.g. 500 kOhms and sweaty skin could be as low as 500 Ohms. This problem may be over come by utilizing a high impedance amplifier, where impedance is above 00 MOhms. The transducer may be designed to activate other system components on the first skin contact thereby ensuring longer lifetime.

The central processing unit (CPU) handles the amplification (e.g. ×30-×1000) of the transducer signal, typically by differential instrumentation amplifier with rejection of common modes (unwanted signals/noise that is common for both electrodes), filtered either analogically or digitally. The CPU handles conversion of analogous signal to digital signal. Signal analysis such as rms (root mean square), FFT (Fast Fourier Transformation) and digital filters combined with software are employed to achieve a data decision on certain events.

Furthermore the CPU could employ timers or sleep mode, so measurement is only during certain events or only a fraction of each second or other time period, thereby saving power.

The microelectronic system also comprises storage components for storage of Software and EMG data storage in those cases where, only some or no data are transmitted wireless during data acquisition. These data may be transmitted at a later time.

The power source is thought to be either a single use battery as the CPU ensures long lifetime due to power down in inactive periods, or a rechargeable battery. The rechargeable battery is recharged either through a RF link or by placing the microelectronic system in a recharge cradle when the system is not in use. Several weeks of lifetime after activation are possible with one battery or charge up.

Data is transmitted to Central Unit with a protocol or method that can ensure no corruption of data. Furthermore after activation battery life condition and/or a data burst are transmitted in order validate operational status of the system. On request the system will transmit storage data.

The microelectronic system for electromyography may optionally include an actuator, which at certain events decided by the CPU activates an alarm in the microelectronic system, such as loudspeaker or LED. The event activating the actuator could also be low battery.

According to this embodiment of the invention the various components are interconnected mechanically and electrically and may be encapsulated into a module. However, various components may also be integrated separately into the adhesive body. These components could be but is not limited to, the battery, the antenna and the actuator.

The various components could also be mounted on PCB (printed circuit board) or flexible PCB and coated with a protective layer and directly be embedded in the adhesive.

Thus, in a specific embodiment of the invention, the microelectronic system is a system useful for electromyography and comprises a transducer (2-3 electrodes and an Instrumentation Amplifier), a CPU (µ Controller e.g. AT EGA 128L), a power source (e.g. battery), communication (e.g. to CU) and storage components and an actuator (LED). This system may be embedded in the adhesive body as illustrated in FIGS. 3 and 3A.

During sport or fitness exercise different or several of the same microelectronic systems may be used in combination. Furthermore several transducers could be used in the same adhesive device.

A fitness sensor network may thus consist of:

Adhesive devices with a muscle activity (sEMU) sensor, one for both sides of the body (arms, legs etc). The electromyography system could be designed in such a way to determine the fatigue of the muscles and indicate when muscle growth is optimal or when exercise has no benefit Frequency analysis of the sEMG signal may be used to achieve the desired output of the measurements. Typically the adhesive devices are placed on muscle groups that are actively exercised.

Two or three adhesive devices of the invention comprising a Heart Rate (ECG) sensor system of for monitoring heart beat and heart pulse shape.

Adhesive devices comprising microelectronic systems for determining levels of fatigue poisons in muscles.

A sensor Hub/gateway centrally located on the body for storing and routing signals to either a central unit or directly communicating with fitness hardware.

The microelectronic system may be reusable from one fitness session to another with change or charge up of battery.

Thus, the adhesive device according to the invention may suitably be used for measuring physiological conditions that relate to diseases, health care surveillance, rehabilitation, sports medicine or general surveillance. Typically applications will be for patients at risk for instance when suffering from weak heart, epilepsy, fever and fever spasms, diabetes, apoplexy, arteriosclerosis and muscular dystrophy. Applications may be associated with general monitoring for optimising medication, for registering of the disease or for alarming. Other applications will be for rehabilitation in respect to monitoring of physical work, muscle strength, lung capacity, or in the sports medicine for determination of work and repetition, acceleration, heart rate, muscular stress and strength, orientation etc. Yet other applications will be for surveillance of objects or mammals in motion. Mentally disable patients or individuals like elderly people suffering from dementia will be typical for such applications.

The adhesive device according to the invention will preferably be wireless as this will be meaningful in respect to obtaining as smooth a shape and surface of the device as possible and still achieving the protection of the microelectronic system. In certain occasions it may, however, be important to be able to interconnect the devices by wires. This may especially be an option when the microelectronic system is divided in two parts each being present in an adhesive device as defined in the invention.

The microelectronic sensing system or the components thereof may be incorporated into the adhesive body either during production of the adhesive body, or after production of the adhesive body, e.g. just prior to application of the adhesive device to the skin, or after application of the adhesive device to the skin.

As described above, parts of the adhesive device such as parts of or the entire microelectronic system may be exchangeable or reusable.

Thus, in one aspect of the invention the present invention discloses a device comprising at least an adhesive element and a power source element, said device adapted to attach an electronic circuit, such as the microelectronic system, to a surface and to power said electronic circuit, wherein at least one of the device elements is releasable attachable to the electronic circuit; the power source element is electrical connectable to the electronic circuit; and the adhesive has at least a first area for adhering to the surface.

Such a device as described may attach and power the electronic circuit to a surface, such as e.g. the skin of a mammal, for a specific purpose. When the specific purpose is fulfilled the device and the electronic circuit is removed from the surface and the device is separated from the circuit and disposed. Thus, the elements forming the device, which are relative cheap compared to the electronic circuit, is disposed while the electronic circuit may be reused together with a new device according to the invention for attaching the electronic circuit to a surface and powering the circuit. Advantageously this allows reducing costs considerably while also protecting the environment as more components are reused than done until now.

By the terms 'releasable attachable' and 'releasable connectable' it should be understood that the device and the electronic circuit may be temporarily attached in such a way that the risk of unintentionally separating them is minimal. However the device and the electronic circuit should be attached in such a way that they may be separated if desired.

Furthermore, by the term 'electrical connectable' it should be understood that the power source element and the electrical circuit is arranged in such a way that an electrical current may be transmitted between them. This may for example be done by use of standard electrical contacts, typically made of copper alternatively gold or silver plated, or the electrical connection may be provided in a wireless manner where the power source induces a current in the electrical circuit.

Typically the electronic circuit is a microelectronic system formed of a number of microelectronic digital components and/or analog components connected with appropriate wiring. The components are typically arranged on a print circuit board whereon the proper traces and tracks are etched, electroplated, or otherwise provided on the board. Digital components may for example be microprocessors, storage elements such as RAM-blocks and analog components may for example be resistors and capacitors provided on the print board.

In one embodiment the power source element is attached to the adhesive element and the adhesive element has a second area for adhering to the electronic circuit.

By attaching the power source element and the adhesive element to each other only one physical part is provided, avoiding that the user has to keep track of both the power source element and the adhesive element and spend time on applying both. Thus a small and discrete device, which is convenient for the user, is provided. Furthermore the electronic circuit may be adhered to the adhesive element for improved handling, as only one unit will have to be manipulated when applying the electronic circuit to the surface.

Advantageously a first peel force between the second area and the electronic circuit is smaller than a second peel force between the power source element and the adhesive element. This allow for easy separation of the microelectronic circuit from the device after use.

To further ensure that the power source element and the adhesive element do not separate from each other the power source element may at least partly be contained in the adhesive element.

By 'contained' it should be understood that the power source may be fully or partly embedded in the adhesive. When fully embedded only electrical contacts are exposed through the adhesive or thin flexible electrical wires are embedded in the adhesive extending from the power source to an outer surface of the adhesive where it may be brought into contact with the electronic circuit. Furthermore, within the meaning of the term contained the power source may also be partly embedded in the adhesive thereby exposing a larger section through the adhesive. This allows for a large contact surface between the electronic circuit and the power source while at the same time being safely attached to the adhesive.

To protect the different parts of the electronic circuit it will typically be encapsulated, for example by coating it in silicone or hot-melt polymers. The encapsulation may for example be formed as a housing containing at least a part of the electronic circuit. In one embodiment the housing may be formed of a proximal housing part and a distal housing part. The device is adapted to be releasable connectable to said housing.

A number of encapsulation techniques are known and includes coating, two component polymer, hot-melt polymer encapsulation, ceramic encapsulation and glass encapsulations. Other methods for encapsulation of electric components are known in the art.

The microelectronic system or components thereof is suitably encapsulated in a polymer film, a polymer foil, or a polymer coating or the microelectronic system or components thereof is moulded into a polymer material, or is encapsulated in a glass or ceramic material.

Encapsulation in silicone, such as PDMS, is particularly preferred when the microelectronic components are to be placed in a through hole or a recess in the adhesive body and where it is desirable to enable easy removal or replacement of the encapsulated microelectronic component(s), as the silicone surface is easily released from the adhesive of the adhesive body. Other materials, which are easily releasable from the adhesive, may also be used for the encapsulation.

In order for the adhesive element to be easily released from the housing after use the housing may advantageously be made from a material, or coated with, which allows the housing to easily release. Such a material may for example be a silicone, which often is used for release liners in different adhesive applications.

In yet another embodiment the at least one power source element is adapted to be received in a recess formed in the distal housing part. At least one electrical contact is provided in the distal housing providing electrical connection between the power source element and the electrical circuit.

By providing a recess as described above the power source element is protected from being displaced and thereby losing electrical contact with the circuit. The recess also creates a flush assembly when the power source is placed therein giving it a smooth surface which will not get caught as easy as from a surface where the power source would protrude.

Many types of electronic circuits having many different applications and which is powered and attached to a surface may be used with the device according to the invention. The device may after use be disposed but the electronic circuit may be reused, in one embodiment the device is thus adapted to be releasable connected to electronic circuit, which is a sensor circuit, said sensor circuit is to be attached to the body surface of a mammal, typically the skin.

By the term 'sensor' or 'sensoring' it should be understood that a parameter of the ambient environment of the electronic circuits is detected by the sensor circuit. Such parameters may among many for example be temperature, humidity, electrical signal, electrical fields, light, noise, biosignals and magnetic fields.

Thus, the invention also relates to a sensor assembly adapted to be attached to the body surface of a mammal, comprising; a sensor circuit, comprising a number of electrical components; at least one power source element for powering at least one of the electrical components; at least one adhesive element for attaching the sensor assembly to the body surface of a mammal; and that at least one of the power source element and the adhesive element is releasable connected to the sensor circuit.

Thus, the sensor assembly provides the advantages as disclosed above when different elements are disposable, such as the device comprising the power source and the adhesive element, and others are reused, such as the electronic circuit.

In one embodiment of the sensor assembly the sensor circuit is at least partly contained in a housing where the housing is formed of a proximal housing part and a distal housing part. Advantageously a sensor assembly may be provided where a first peel force between the adhesive and the housing is smaller than a second peel force between the adhesive and the battery. This allows for easy separation of the sensor circuit from the adhesive and power source elements.

Typically the sensor assembly will comprise at least one transducer attached to a proximal surface of a proximal part. Together with a distal part the proximal part makes up a housing, as described earlier, for protecting at least a part of the sensor circuit. This transducer will transform different physiological signals into electrical signals. Such transducers may for example potentiometric, caliometric, conduemetric, chemomechanical or optical.

To prevent that the power source accidentally moves out of electrical contact with the sensor circuit a recess may be formed in the distal housing part, the recess is adapted to receive the at least one power source and that at least one electrical contact is provided in the distal housing providing electrical connection between the at least one power source and the electrical components. The recess thus protects the power source from outside movement, for example when the adhesive moves due to movement of the surface whereto the sensor assembly is attached. Additionally, by protecting the power source from outside movement the electrical connection between the power source and the microelectronic circuit is also protected from disconnection.

In another aspect the present invention relates to the use of a device comprising an adhesive element and a power source element, and where the device is used for attaching an electronic circuit to a surface and to power said electronic circuit, wherein said electronic circuit is releasable connectable to the adhesive element and the power source element.

Many sensors are connected to the monitoring systems with wires. The disadvantage of such a system is that the patient does not have freedom to move since the wires are attached to the sensors on the body and connected to a monitoring system. Whenever the patient wants to move he must be careful not to dislodge any of the wires attached to the sensors, and he must further pick up the monitoring system and carry it along.

Furthermore, an isolated power source, such as a battery, where no external wiring is necessary is preferred. Such isolated power source elements preferably used with the present invention are well known in the art.

In general, batteries may be divided into primary batteries, which are single use and secondary batteries, which are rechargeable.

Primary batteries are produced in various types based on different combinations of anode, cathode and electrolyte materials. Common chemistries for primary batteries include zinc-carbon, zinc chloride, alkaline manganese dioxide, silver oxide, zinc/air and lithium in these combinations: lithium/sulfur dioxide (Li-SO2), lithium/thionyl chloride (Li-SoCL2), lithium/manganese dioxide (Li-MnO2), lithium/carbon monofluoride (Li-(CF)n), lithium/copper oxide (Li-CuO), and lithium/iodine (Li-I2).

Secondary batteries are rechargeable and are typically based on Nickel Cadmium (NiCd), Nickel Metal Hydride (NiMH) or Lithium-ion technologi. Secondary batteries usually have more active chemistries that need special handling and disposal.

Many battery sizes and cell casing exist, including standard cylindrical cells, multi-cell batteries, coin cells, pouch cells and thin film batteries.

Standard cylindrical cells and multi-cell batteries are known from common household appliances, e,g. flash lights and remote controls. This group includes the well known sizes AA, D, C, and 9V rectangular.

Coin or button cells are typically small, round and a few millimetres high. This group is often found in watches, hearing aids and memory backup. Since they are based on solid-state cathodes, these systems are considered very safe.

Duracell, Panasonic, Sony and Energizer are some of the major manufacturers of standard and coin cell batteries.

Alternatively, using pouch casings along with Lithium Polymer cells with solid electrolytes can provide another type of batteries. This provides a low cost bendable construction. The batteries are characterized by a high energy density in addition to being re-chargeable. The solid electrolyte permits safer, leak-proof cells. The foil construction allows very thin and lightweight cell designs.

Bullith Batteries manufactures flexible batteries based on this technology.

Yet another type of batteries are thin film batteries, which are based on the printing of solid state lithium polymer chemistry on a variety of substrates. They can be printed directly onto plastics, thin metal foils or paper resulting in ultra thin and flexible power sources. The batteries can be made in any shape or size, but are generally limited in energy storage and current capacity. The batteries are very safe as they contain no caustic chemicals, cannot overheat, explode or cause electrical shock.

The Israeli company Powerpaper are selling products based on thin film technologies. Other companies producing this type of batteries are Oak Ridge Micro Energy Inc. and Infinite Power Solutions.

In one embodiment the adhesive element is formed as a three-dimensional adhesive body as described earlier, i.e. the adhesive element has a considerable thickness, typically several times thicker than the backing layer whereon it is applied.

The pressure sensitive adhesive making up the three-dimensional adhesive body is suitably a mouldable thermoplastic or chemically curing pressure sensitive adhesive having a flexibility enabling the adhesive device to conform to the curvature of body parts while retaining its adhesive properties even under movements.

The backing layer may furthermore function as a cover layer, where said backing/cover layer is provided to function as base wherein the adhesive is applied and to protect the adhesive from the outer environment, e.g. against adhesion to linen, clothes or moisture.

Furthermore, an electromechanical display system may be applied to the cover layer. Such display system may allow the user to test the charge of battery either before adding the powered adhesive to a microelectronic system and during use.

Simple battery indicators known in the art may thus be used. For example a foil consisting of two contact electrode and a conductive thermochromic ink, typically liquid crystals or leucodyes, may be used.

When for example using a common coin battery, one electrode is in contact with the anode of the battery and the other electrode in contact with cathode of the battery. By pressing the contact device on top of battery the battery test circuitry is closed and the thermochromic ink will light up indicating battery status.

The cover layer or film protects the integrated/embedded microelectronic components as well as the adhesive body against the environment.

The adhesive device of the invention may be constructed in a number of ways, as it will be described in more detail below. Common for all constructions are that the three-dimensional geometries provide good protection for the microelectronics and at the same time give the device as smooth a surface as possible. Especially the shaping of the edges of the device need paid attention, otherwise linen will easily stick to them and cause rolling. Therefore the outer rim of the adhesive device with the embedded micro electronic system must be shaped to thickness less than half of the thickest part of the device, normally the central part comprising the microelectronic electronic system.

DETAILED DESCRIPTION OF THE DRAWINGS

FIG. 1 shows a die section of the shape of a typical representative of the adhesive device according to the invention. CT relates to the maximal thickness of the device and PT to the thickness in the periphery of the device. The device does not necessarily need to be shaped symmetrically.

FIG. 2 has a box showing the part of the adhesive device, which is illustrated in FIGS. 3-12. As illustrated in FIG. 2 the electronic parts 101 are embedded in an adhesive body 102 with a cover layer 103 and a release liner 104.

In one embodiment of the invention, all the electrical components are assembled in one unit, which is embedded in the adhesive body and is covered on all sides with the pressure sensitive adhesive, essentially making it a disposable pad. As illustrated in FIG. 3 an assembly of electronic parts 101 are embedded in an adhesive body 102 with a cover layer 103 and a release liner 104.

FIG. 4 illustrates that the components of the microelectronic sensing system may be positioned at different locations within the adhesive body, provided there is the required mechanical or electrical connection between the components. All components are completely embedded in the adhesive body and are covered on all sides by the pressure sensitive adhesive of the adhesive body.

The integration of all microelectronic components within the adhesive body is useful for cheap throw away one time one use devices. Because of the short usage time of the adhesive device the electronics need little or none extra protection, such as encapsulation. The adhesive body itself acts as protection of the microelectronic components.

Even though all the components of the microelectronic system are covered on all sides with the adhesive body, several sensing applications (humidity, optical or chemical/gas) are still possible.

Systems, which may be covered on sides, may also be a RFID TAG, a Network Hub, a network coordinator, a gateway, or other systems capable of collecting, communicating and/or transmitting data. These systems would often need some kind of activation to start the system, such as a pressure contact or magnetic contact to overcome the need for large shelf life compared to the active period.

FIG. 5 illustrates an embodiment of the invention where the microelectronic system is embedded/applied into a recess in the adhesive body. The recess is positioned in the upper surface of the adhesive body. The microelectronic system may be embedded/attached during fabrication of the adhesive body, just before or after the adhesive device has been attached to the skin. According to this embodiment of the invention, the microelectronic system may be reused.

FIG. 6 shows a microelectronic system analogous to the system of FIG. 5, however, in FIG. 6 the system consists of two parts. One part, the upper, is exchangeable of reusable and the lower is embedded in the recess of the adhesive from start. The upper part may for instance be the power supply.

FIG. 7 illustrates an embodiment where some components of the microelectronic system is embedded within the adhesive device during production and some components are applied in a recess in the upper surface of the adhesive body, i.e. are exchangeable or reusable. According to the invention one or more component(s) may be embedded within the adhesive body and one or more component(s) may be present in a recess at the surface of the adhesive body. The necessary mechanical or electrical connection between the components are also embedded in the adhesive body. Although the figure only illustrates one, there may be two or more recesses in the upper surface of the adhesive body and there may be two or more components integrated into the adhesive body.

The exchangeable parts in the recess may be locked in the recess by the adhesive properties of the pressure sensitive adhesive in the recess. In an alternative the microelectronic components in the recess is encapsulated in a coupling or plug designed to fit into a lock, such as a snap lock, present in the recess.

FIG. 8 illustrates an embodiment of the invention where the microelectronic system is embedded/applied into a recess in the adhesive bottom surface of the adhesive body. The microelectronic system is embedded/attached during fabrication of the adhesive device or just before attaching the adhesive device to the skin. This system is typically used where it is required that some of the components of the system are in contact with skin either non-invasively or invasively.

FIG. 9 illustrates en embodiment where some components of the microelectronic system is integrated within the adhesive device during production and some components are applied in a recess in the lower surface of the adhesive body, i.e. are exchangeable. According to the invention one or more component(s) may be integrated into the adhesive body and one or more component(s) may be present in a recess at the surface of the adhesive body. The necessary mechanical or electrical connection between the components are also integrated into the adhesive body. Although the figure only illustrates one, there may be two or more recesses in the bottom surface of the adhesive body and there may be two or more components integrated into the adhesive body at different locations.

FIG. 10 illustrates an embodiment where some components of the microelectronic sensing system is integrated into the adhesive device during production and some components are applied in a recess in the bottom surface of the adhesive body, i.e. are exchangeable or reusable. According to the invention one or more component(s) may be integrated separately into the adhesive body and one or more component(s) may be present in a recess at the surface of the adhesive body. Although the figure only illustrates one, there may be two or more recesses in the bottom surface of the adhesive body.

This construction is suitable where the transducers or actuators utilize skin contact or skin penetration (e.g. electrodes and needles), whereas the rest of the microelectronic system may be embedded in the adhesive body (batteries, antenna, electrode, A/D converter, amplifier). This configuration also has several production advantages.

Thus, FIGS. 8, 9 and 10 illustrates a construction where the exchangeable part e.g. the battery, is attached to the adhesive part facing the patient. Prior to mounting the adhesive sensor device on dermis of the mammal the protective release liner is removed, the exchangeable battery is coupled to the rest of the microelectronic system enabling the electronic system to function. Thereafter the adhesive part of the device and the whole construction is mounted on the dermis of the patient.

After use the exchangeable part e.g. the battery, is replaced and the adhesive device may be used in the context of a new monitoring of the patient.

In order to be able to remove the battery following detachment of the adhesive device, the inner part of the recess in the adhesive device could be coated with a PDMS curable coating or other non-adhesive coating; this operation will facilitate the exchange of the battery.

The battery as well as other exchangeable components, such as the chip, may be present in a recess in the bottom surface of the adhesive body. According to this embodiment, it may be an advantageous to have the exchangeable microelectronic parts contained in a capsule, e.g. embedded in an injection-moulded capsule.

Just prior to mounting the capsule containing the microelectronic components the release liner is removed and the exchangeable capsule is attached to the adhesive body in the recess of the adhesive construction. The microelectronic components may be coated with curable PDMS or other non-adhesive coating in order to facilitate detachment of the exchangeable capsule.

When the microelectronic components have a longer life than the adhesive body, the cheap components, such as the transducer, the antenna or the power source, may be integrated into the adhesive body and the components that may be reused are placed in a recess before use.

Another application is where customised preparation or programming of the system is done prior to application.

The features and applications described in connection with FIG. 3 apply equally well to the embodiment illustrated in FIG. 5 and vice versa.

FIG. 11 illustrates the integration of a microelectronic system within a through hole in the adhesive body providing access to the microelectronic system from both the upper surface and the bottom surface of the adhesive body. The application of the microelectronic system is possible both during production/fabrication of the adhesive or just prior to application to the skin, and/or after application to the skin.

FIG. 12 illustrates a system where two components or assemblies of components of the microelectronic system are connected in some way. One of the components may be integrated during production, whereas the other is applied afterwards.

Alternatively, the components or assemblies of components are applied afterwards. This is useful where different lifetime make is feasible to exchange electronic components at different times, such as battery or transducer. Mechanical and/or electrically interconnection schemes such as snap locks or plugs are advantageous in this configuration.

The system illustrated in FIG. 4 is useful where skin contact and simultaneous access to electronic components from the upper surface is needed. One or both subsystems can be reused.

The features and applications described in connection with FIGS. 5 and 8 applies equally well to the embodiment illustrated in FIG. 11 and vice versa.

FIGS. 13-18 illustrates an embodiment of the invention where an antenna, a central processing unit, a battery and electrodes are embedded in an adhesive device.

FIG. 13 illustrates the two-dimensional shape of the device indicating a cross-section by A-A.

FIG. 14 illustrates the position of the antenna 109 placed in the outer part of the adhesive device and being connected to the central part of the microelectronic system.

In FIG. 15 the third dimension is shown in cross-section along the line A-A in FIG. 13. The circle B from the rim of the device is further magnified in FIG. 16 and the circle C of the centre is likewise magnified in FIG. 17.

FIG. 16 shows more in detail the building of the antenna lying embedded in the adhesive. This clearly shows the cover film 103 and the release liner 104 for the adhesive 102.

FIG. 17 shows the position of the central part of the microelectronic system I with a battery 105, a CPU 106 and protruding the adhesive the electrode 107. The battery and the CPU is enveloped in a transparent silicone rubber 108.

Finally FIG. 18 illustrates the adhesive device in a perspective.

There are other ways of constructing an adhesive device having an embedded micro electronic system, that fulfills the basic requirement of a three-dimensional construction and the drawings may thus not be construed as limiting.

One special advantage of the invention is the simple and inexpensive way of preparing an adhesive body having a three-dimensional shape from a pressure sensitive adhesive.

As mentioned above, the pressure sensitive adhesives are either a thermoplastic pressure sensitive adhesive or it is a chemically curable adhesive that has the ability to be moulded into a three-dimensional shape.

The thermoplastic pressure sensitive adhesive may typically enter a fluid condition and achieve a moderate viscosity at above 100-120 deg C i.e. above the glass transition temperature of the composition, which makes it easy to mould the adhesive composition to the desired shape. One example may be direct moulding. In a first step the cover layer is provided in the desired shape at temperatures just below the glass transition temperature of the cover film and then the necessary amount of adhesive is filled the into the mould to fill up the mould. The filling of the mould may be in two steps whenever appropriate. This will allow partly filling with the molten adhesive in a second step, placing the electronic parts in a third step and eventually filling and covering the electronic parts with the remainder of the adhesive in a fourth step. As a last step a release liner is applied and then the adhesive device is punched out of the mould.

Alternatively the adhesive laminated with the cover film may be processed through compression, pressing or moulding into the desired geometry or shape at elevated temperature, but slightly below the glass transition temperature of the adhesive. Optionally the microelectronic system may be placed between two layers of adhesives and then moulded. The moulding is performed in the press at elevated temperature and if desired with the microelectronic system placed in the mould preferably in the centre of the mould.

In the special embodiment where exchangeable or reusable components are a part of the adhesive device, a female and a male part of a moulding shape is required.

In another embodiment of the invention curable pressure sensitive adhesive is cast in the desired shape. The casting may follow the same principles as of above allowing a partial filling step of the mould with the cover film, applying the electronic components and thereafter complete the filling of adhesive in the mould and finally concluding with placing the release liner, curing if necessary and die cutting.

Another method is moulding by compression of adhesives having high or very high viscosity. A primary layer comprising a pressure sensitive adhesive e.g. a hydrocolloid containing block copolymer on a cover film taken from a roll enters the processing equipment as a first step, the pre-assembled, optionally encapsulated micro electronic components is placed with the appropriate distance in a second step, in a third step, a secondary layer of the same or another pressure sensitive adhesive is laminated to the first layer of pressure sensitive adhesive enclosing the microelectronic part between the layers, in a fourth step said laminate is formed in a hydraulic press into a shape containing multiple projections centred upon the microelectronic part and in a fifth step the individual projections are die cut to final devices.

The pressure sensitive adhesive devices can be produced according to a continuously process as described in U.S. Pat. No. 6,726,791.

FIGS. 19, 20 and 21 shows one embodiment 1 of a sensor assembly according to the invention. FIG. 19 shows the sensor assembly in an exploded view. FIG. 20 shows the assembly seen in section along line XX-XX in FIG. 19 when the sensor assembly is assembled. FIG. 21 shows the sensor assembly seen from the skin side, also referenced to as the proximal side, i.e. the side of the sensor assembly, which is to be attached to the skin.

The sensor assembly 1 consists of a sensor device 2 and housing element 3 which contains a microelectronic circuit 4. The sensor device 2 is made up by an adhesive element 5 and a power source element in the shape of a coin cell battery 6.

The housing element 3 is made up of a distal part 7 and a proximal part 8. A recess 9 is formed in the distal part. The recess has a circumference, which is slightly larger than the circumference of the coin cell battery allowing the coin cell battery to be received in the recess.

In the recess there is provided two electrical contacts 10a,10b for electrically connecting the microelectronic circuit 4 and the battery 6 when the battery is placed in the recess. The microelectronic circuit is made up of a number of components arranged on a print board 11. Every component will not be described herein as the circuit is well known in the art and as such not a part of the invention in itself. In general it can be mentioned that the circuit comprises an antenna 12 formed by a number of windings of a conductive material printed on the print board. The antenna transmits and receives data from a central unit placed within communication range. The central unit may for example be a personal computer which gathers data from the sensor assembly. The data is then processed according to known processes and algorithms.

The antenna 12 is connected to a microprocessor 13, which receives signals from a first transducer 14 and a second transducer 15. The first and second transducer extends from the print board through the proximal part and terminates on the proximal surface of the proximal part. Thus, when the housing is placed on the skin the first and second transducer contacts the skin surface. In order to reduce interference between the first and second transducer a barrier element 16 is placed on the proximal surface of the proximal part between the two transducers. The barrier element is formed of a dielectric material and is a well known measure in order to avoid so-called cross talk, typically causing unwanted interference, between two electronic components.

When used the battery is placed in the recess, whereby the battery is placed in contact with the electrical contacts 10a, 10 b and thereby powers the microelectronic circuit. The adhesive element is then applied on the distal side of the distal part of the housing and the distal side of the battery. This secures the battery in the recess and connects the adhesive element, the power source element and the housing element into a sensor assembly.

As can be seen the adhesive element has a circumference which is larger than the circumference of the housing which provides an adhesive proximal surface 17 which can be applied to the skin surface of a person or other mammal.

When the sensor assembly later is removed the adhesive element is separated from the housing element the battery is removed along with the adhesive element as the distal surface of the battery is adhesively attached to the adhesive element. The adhesive element and the battery can then be disposed and the housing element may be cleaned and stored for later use.

The adhesive element is covered by a cover layer 18 in order to protect the adhesive element from adhering to unwanted surfaces, such as the inside of worn clothing articles. The cover layer 18 also functions as backing layer whereon the adhesive material 19 is disposed during production.

FIG. 22a shows another embodiment 30 of a device according to the invention. FIG. 22b shows a section of FIG. 22a in an enlarged view. The device is made up by a two-dimensional adhesive element 31 and a power source in the shape of a coin cell battery 32 adhered to the adhesive element.

The adhesive element is formed of a backing layer 33. On the proximal side of the backing layer there is provided a first adhesive layer 34, which is covered by a first release liner 35. The distal side of the backing layer there is provided a second adhesive layer 36 to which the battery is adhered. A second release liner 37 covers the rest of the distal side of the adhesive, whereon the battery is not attached, When applied to a surface, such as a skin surface of a person, the first release liner 35 is removed. This exposed the first adhesive layer, which may be adhered to the skin surface thereby attaching the device 30 to the skin surface. The second release liner is then removed exposing the second adhesive layer. Not shown in the drawing, a housing containing a microelectronic system is then attached to the adhesive layer while at the same time an electrical contact on the housing is brought into electrical connection which the battery 32.

Although such a housing as described above do not have any surface contact such as the housing described with reference to FIG. 19, the housing may still comprise sensor technology. Such sensors may simply measure the ambient temperature or the device may be applied under the nose and a sensor for measuring the breathing rhythm through the nose may be applied on the device. Alternatively the sensor may apply skin contacting transducers outside the circumference of the device, while still being adhered thereto.

FIG. 23 shows yet another embodiment 40 of a two-dimensional device according to the invention and FIG. 24 shows a sectional view of the third embodiment along line XXIV-XXIV in FIG. 23. Here the power source element is formed as a thin film battery 41 being an integrated part of a backing layer 42.

On the proximal side of the backing layer there is applied a first adhesive layer 43 which is covered by a first release liner 44. The distal side of the backing layer is covered by a second adhesive layer 45 which is covered by a second release liner 46. The second adhesive layer is interrupted in an area 47 allowing access to contacts 48a and 48b which provides electrical contact to the thin film battery.

When used the device 40 described with reference to FIG. 23 is applied in the same way as the device 30 described with reference to FIG. 22.

It should be understood that different types of adhesives may be used on respectively the proximal side of the backing layer and the distal side of the backing layer. While the proximal side is attached to the skin surface and thus preferably should be skin friendly, the adhesive on the distal side should preferably be of a type which provides optimal attachment to a electronic circuit or a housing containing such circuit while still allowing the device to be separated there from after use.

Although the above embodiments describe releasable attachable means in shape of adhesive attachment for connecting the device to the electronic circuit other types of release attachable means may be used. Such releasable attachable means can for example be mechanical such as a snap lock arrangement between the battery and the recess in the housing, where the recess is formed with protruding ribs which couples with the battery. Alternatively additional coupling means may be provided on the device for coupling with complementary coupling means on the electronic circuit or the housing containing the electronic circuit, and may for example be in the shape of bayonet coupling, hooks, frictional couplings or threaded couplings.

Experimental Section

EXAMPLE 1

Three batches of adhesive were produced. The adhesives were prepared by standard hot melt procedure in a Herman Linden z-blade mixer (Machine type LK I 110.5), by mixing the components of elastomer (Kraton), one third of the plasticiser (DOA) and the resin (Arkon) at 130 degree C. until a homogeneous mixture was achieved (30-50 minutes). The rest of the plasticiser and the hydrocolloid filler (CMC) was added and the mixture was blended for 20 minutes.

|  | Recipe 1 | Recipe 2 | Recipe 3 |
| --- | --- | --- | --- |
| Kraton 1161 (Shell) | 18.0 | 19.0 | 15.0 |
| Arkon P90 (Arakawa | 32.0 | 36.0 | |

-continued

|  | Recipe 1 | Recipe 2 | Recipe 3 |
|---|---|---|---|
| DOA (Dioctyl adipate) | 5.6 | 7.5 |  |
| Vistanex ® LM-MH (Exxon) |  |  | 45.0 |
| CMC: Blanose 9H4XF (Hercules) | 44.4 | 37.5 | 400 |

EXAMPLE 2

Moulded Bodies of the Adhesives of Example 1:

Each of the adhesives according to claim 1 were applied on to a 35 micrometer thick cover film of polyethylene and a siliconised polyethylene liner was applied to the opposite side of the adhesive patch and pressed to the desired shape according to any of the illustrations 1-3 in a for the shape designed mould at 90 degree C. by altering the non-cavity holding mould to give the shape of the recess. The centre of the adhesive device was 3.4 mm and the thickness of the outer rim 0.4 mm.

EXAMPLE 3

Moulded Silicone Pressure Sensitive Adhesive Body:

Dow Corning 7-9800 A&B (mixing ration between A and B is 1:1 by weight) were used for production of a PDMS based adhesive body. A mould having a triangular shape (each side of the triangular mould having a distance of 300 mm, the center part having a thickness of 0.5 mm and the edge having a thickness of 0.1 mm) was used. The components were thoroughly mixed and applied on a 50 μm cover layer of silicone rubber lining in the female part of a triangular mould and a male mould part was placed on top, said part lined with a low density polyethylene release liner. The adhesive was cured in an oven at 100 degree C. for 15 minutes. After curing the adhesive was punched out of the mould and a dent in the centre of the adhesive body device for embedment of an electronic sensing system was punched out.

EXAMPLE 4

Moulded Thermoplastic PSA Adhesive Body:

The components of recipe 2 in example 1 were mixed in a Herman Linden mixer and while still hot and soft, the resulting dough-like material mass was removed from the mixer and placed on a thermoplastic polyurethane cover film placed in the cavity of a moulding form and a release liner is placed on top. The second part of the mould was plane. The adhesive is compression moulded at approximately 90 degree C. and 100 bar. The release liner was removed and an encapsulated microelectronic sensing system was placed at the centre of the adhesive body within the mould, the release liner was reapplied and the moulding step was repeated. Finally the resulting sensor pad was punched out.

EXAMPLE 5

Moulded Thermoplastic PSA Adhesive Body with Integrated RFID-Tag:

A pressure sensitive adhesive according to recipe 2 in example 1 were mixed in a Herman Linden mixer and while still hot and soft a minor part of the material was removed from the mixer and placed on a cover film towards the female part of a mould and a release liner was placed on top and thereafter the male part of the mould having a small protrusion over the area corresponding to the microelectronic system of the product was applied. The whole construction is compression moulded at approximately 90 degree C. and 100 bar. Hereafter the release liner was removed and a RFID tag encapsulated in polypropylene was placed in the recess of the pressure sensitive adhesive and the mould was filled up with the remaining adhesive. A release liner is attached again and the whole construction was compression moulded again. The resultant pad was punched out. The thickness of the outer rim was 0.2 mm, the central thickness was 2.5 mm and the shape was circular with a diameter 40 mm.

EXAMPLE 6

In this example the micro electronic system embedded into the adhesive body consist of both the RFID tag and communication and storage components. In order to protect the micro electronic system the components are encapsulated in poly:ethylene. The components are integrated in the PSA during a continuous process as described in. U.S. Pat. No. 6,726,791. The primary layer comprises the cover film with pressure sensitive adhesive, the secondary layer is the encapsulated micro electronic part; and the third layer is of a mouldable layer pressure sensitive adhesive; the whole construction is combined in the moulding cavities.

EXAMPLE 7

Preparation of a Hydrogel Adhesive Composition:

3,5 grams of PVP K-90, 17.5 grams of PVP K-25, 3.5 grams of Pemulen TR2 and 28 grams of PEG 400 were mixed as a premix. Initially the premix of the plastizicing glycols, the PVP and the cross-linked polyacrylic acid were added and mixed in a Brabender mixer at 100 degrees C. for 10 minutes. Then 17.5 grams of the amphiphilic polyurethane (Tecogel 2000) was slowly added in order to ensure complete mixing of the components. After 20 minutes' mixing a macroscopically homogenous mixture was obtained. The hot adhesive from the mixing chamber was moulded into a circular adhesive body (diameter 4 cm) with a dent for a later applied micro electronic system. The thickness of the pad is 3 mm at the centre and the thickness is gradually decreasing to 0.3 mm at the edge of the pad. The adhesive device was compression moulded between a sheet of silicone paper and a 30 mm PU cover film.

EXAMPLE 8

A microelectronic Sensing System for Invasive Measurement of Oxygen;

An adhesive according to example 1 recipe 2 was used embedment of a micro electronic system consisting of an oxygen electrode, a central processing unit, a transmitter and a battery. The shape of the adhesive body is oval (70×30 mm) having a centre thickness of 5 mm, an edge of 0.3 mm and an essential linear increase in thickness from the edge to centre of the pad. The adhesive body has a centrally placed through hole and a dent in the skin-contacting part of the surface of the adhesive body for the silicone covered micro electrical components.

The CPU, the battery and the transmitter are as described in the examples 11. The oxygen electrode was oxygen electrode product number 723 (from Diamond General, Development Corp. US).

The CPU, transmitter and battery were electrically connected and thereafter covered with a thin layer of polymeric silicone, only the electric& contact of the CPU to the electrode, remains uncoated.

The tip of the electrode in the sensing device is surrounded with a medical needle with outer diameter of 0.7 mm.

During use the electrode and the needle are positioned in a way where the electrical contacts of the CPU are connected with corresponding contacts of the electrode.

During application of the measuring device the partly silicone covered micro electronic system was firstly applied onto the adhesive body in the dent at the skin contacting side of the device. The device is applied to the skin. The needle is then positioned from the outside through the hole in the adhesive by penetrating the skin in a second step and the electrode partly enveloped in a plug is mounted through the hollow centre of the needle as a third step creating electrical contact to uncoated connections of micro electronic system. The plug part of the electrode fits the smooth curvature of the cover film without introducing recesses.

During use, the electrode may be rinsed and reapplied according to needs for achieving correct signals.

EXAMPLE 9

Microelectronic Hub Embedded in Adhesive Sensor Device According to the Invention:

An adhesive according to example 1 recipe 1 was moulded in a first layer forming an oval shell (50×80 mm) having a smooth surface to one side. This surface is declining in slope towards the outer periphery and is covered with a 30 μm thin film of polyurethane i.e. placed between mould and adhesive. The opposite side of the adhesive body was formed with a centrally soft shaped indentation of approximately 2×10×15 mm for applying the microelectronic system. A siliconised release liner of polyethylene was placed on the surface with the indentation. In a second step the release liner was removed, an antenna is placed at the outer periphery of the adhesive body and the CPU and the battery was placed in the central indentation. In a final step a second layer of adhesive was applied to embed the antenna at the area of the outer periphery but not the components in the central indentation. A release liner is applied and the complete construct which was die cut to the final size. The antenna is connected to the central microelectronic parts through electrical contacting elements making reuse of the central part possible. The antenna is encapsulated in thin polyethylene terephthalate (PET)-plastic and the central microelectronic parts are encapsulated in silicone rubber.

EXAMPLE 10

Microelectronic Hub:

A construction with microelectronic hub in which the antenna as well as the battery is completely integrated in the pressure sensitive adhesive of previous example 1. This is done by letting the adhesive of the final step in example 9 cover the antenna as well the central microelectronic parts.

EXAMPLE 11

An Adhesive Device Having Embedded a Microelectronic System for Human Temperature Sensing and Alarm with no Remote Communication An adhesive according to example 1 recipe 2 was used for embedment of a micro electronic system consisting of an temperature sensor, a central processing unit, a transmitter, battery and an OLEO (Organic Light emitting Diode). The shape of the adhesive body is round (30 mm) having a centre thickness of 5 mm, a peripheral edge of 0.2 mm and an essential linear increase in thickness from the edge to centre of the pad. The adhesive body has a dent in the skin-contacting part of the surface for the silicone covered micro electrical components.

The CPU is a μ Controlier ATMEGA 128L, an AVR 8 bit RISC processor from ATMEL, Battery is an Panasonic Coin cell CR3202.

OLED flexible colour display is from OSD (One Stop Display) part # OSCC 130-0. Temperature sensor is from Pasport Ps-2125.

During use the temperature sensor continuously monitors human skin temperature. At certain events determined by the micro-Controller influenced by time of day, temperature gradient compared to stored data, the system will give a visual alarm in form text or lights of relevant information at the flexible display.

The system is integrated into the adhesive and activated when peeling off the release liner and will function until end of battery.

EXAMPLE 12

An adhesive device having embedded a microelectronic system for human temperature sensing and alarm with no remote communication is constructed according to example 11.

The construction of the adhesive device is identical to the one of example 11 except that instead of the OLED flexible colour display for signalling a temperature change an EL (Electro-lumiscent Lamp) is used as the signalling part in the surface of the device. The part is an EL Lamp Part #: 300210 KIT from Being Seen Technologies.

During use the temperature sensor continuously monitors human skin temperature. At certain events determined by the micro-Controller influenced by time of day, temperature gradient compared to stored data, the system will give a visual alarm in the form of a light.

EXAMPLE 13

In one embodiment illustrated with reference to FIGS. 19-21 the adhesive material 19 is a pressure sensitive adhesive (PSA) consisting of a hot-melt processable styrenic block copolymer with hydrocolloids, the battery is a metal cased coin cell battery and the housing is coated with a layer of PolyDiMethylSiloxane.

In Example 13 below, the peel forces between the PSA and the surface, the battery and the housing were determined:

The PSA is a hot-melt processable Styrenic block copolymer with hydrocolloids, which is thermo formed into the desired shape. The PSA designated A, has the following composition: 25% Kraton D1107 (Kraton Polymers), 35% Arkon P90 (a hydrogenated polycyclopentadiene from Arkawa Ltd.) 8% DiOctylAdipate and 32% sodium carboxymethylcellulose.

In order to illustrate the peel force between the different parts the peel force has been determined via use of FINAT; FTM2, 25 mm test sample width, 90 degrees peel angle, test speed of 300 mm/min and a resting time of 30 minutes.

With regard to peel force from skin the following test method was utilized:

Strips of adhesive 25 mm wide were cut from slabs of PSA composition A. A strip of adhesive tape (TESA 4124) was attached in order to prevent stretching of the samples. The samples were taped to a clamp. The skin of the volunteer was prepared by washing the underside of the forearm with diluted soap and allowing to dry at least 2 hours before the PSA was attached. The adhesive side of the sample was placed on the prepared skin. The resting time for the adhesive was 30 minutes. The clamp was attached to the hook of the testing device, an instron Tensile tester Model 5564. The forearm was placed on a movable support of the testing device, taking care to keep the end of the sample directly under the clamp in order to keep a 90-degree peel angle. The forearm was kept still while the tensile strength tester was activated to pull the adhesive up at a rate of 300 mm/min. The peel value of the steady state part of the resulting graph was recorded and it was confirmed that no residue was left on the skin of the forearm.

The battery was a metal cased Manganese Dioxide Lithium coin cell battery CR2330, from Panasonic, and the microelectronic housing was coated with a layer of PolyDiMethylSiloxane (PDMS); MED-1137 from NuSil Technology.

The peel forces have been determined between the adhesive and the following parts with following results and with three repetitions of the test, where s indicates the standard deviation.

| | |
|---|---|
| Peel force between A and PDMS coated housing | 0.1 N/25 mm |
| Peel force between A and steel | 22.5 N/25 mm (s = 2.3) |
| Peel force between A and human skin | 2.5 N/25 mm (s = 0.25) |

Furthermore, different types of materials may be used for different parts of the device and the microelectronic circuit and/or the housing whereby different peel forces may be provided. Thus it would be possible to achieve peel forces between the PSA and the skin in the general range of 1-5 N/25 mm, peel forces between the PSA and the housing generally below 1 N/25mm and the peel forces between the PSA and the metal casing of the battery generally above 20 N/25 mm.

It can thus be understood, that when the sensor assembly 1 has been applied to the skin of a user it may easily be peeled off after use, by pulling the adhesive element with a force above the peel force between the PSA and the skin. The adhesive element 5 may then easily be separated from the housing element 3 containing the microelectronic circuit 4. As the peel force between the adhesive element and the battery 6 is much higher than between the adhesive element and the housing, the battery is practically inseparable from the adhesive element, and thus the battery will be attached to the adhesive when the adhesive is separated from the housing.

The invention being thus described, it will be apparent that the same may be varied in many ways. Such variations are not to be regarded as a departure form the spirit and scope of the invention, and all such modifications as would be recognized by one skilled in the art are intended to be included within the scope of the following claims.

We claim:

1. A sensor assembly adapted to be attached to the body surface of a mammal, comprising:
    an encapsulated sensor circuit including a plurality of electrical components arranged on a printed circuit board, wherein the plurality of electrical components includes an antenna and a microprocessor, wherein the encapsulated sensor circuit is encapsulated in one of a polymer film, a polymer foil, a polymer coating, a glass, or a ceramic material, and wherein the encapsulated sensor circuit has a proximal portion and a distal portion, the proximal portion of the encapsulated sensor circuit being configured to couple to the body surface of the mammal;
    at least one power source for powering at least the antenna and the microprocessor of the encapsulated sensor circuit;
    an adhesive device including at least one adhesive for attaching the sensor assembly to the body surface of the mammal, wherein a portion of the adhesive device extends distal to the distal portion of the encapsulated sensor circuit, the adhesive device being adhesively coupled to, and contacting, the at least one power source in a first contact area and being adhesively coupled to, and contacting, the encapsulated sensor circuit in a second contact area, wherein the adhesive coupling between the adhesive device and the power source resists greater pull force than does the adhesive coupling between the adhesive device and the encapsulated sensor circuit, and wherein the adhesive device does not include electrical contacts; and
    a housing at least partially containing the encapsulated sensor circuit, the housing having a recess adapted to receive the at least one power source, wherein the housing is formed of a proximal housing part and a distal housing part;
    wherein the first contact area is less than the second contact area.

2. The sensor assembly according to claim 1, wherein the adhesive is applied to the distal side of the housing and the distal side of the at least one power source.

3. The sensor assembly according to claim 2, wherein at least one transducer is attached to a proximal surface of the proximal housing part.

4. The sensor assembly according to claim 1, wherein at least one transducer is attached to a proximal surface of the proximal housing part.

5. The sensor assembly according to claim 2, wherein at least one electrical contact is provided in the distal housing part providing electrical connection between the at least one power source and the electrical components.

6. The sensor assembly according to claim 1, wherein at least one electrical contact is provided in the distal housing part providing electrical connection between the at least one power source and the electrical components.

7. The sensor assembly according to claim 1, wherein the housing comprises a polymer surface at the second contact area.

8. The sensor assembly according to claim 7, wherein the housing comprises PolyDiMethylSiloxane (PDMS) at the second contact area.

9. The sensor assembly according to claim 8, wherein the adhesive device is coated with a pressure-sensitive adhesive.

10. The sensor assembly according to claim 9, wherein the pressure-sensitive adhesive comprises hydrocolloids or foamed adhesive.

11. The sensor assembly according to claim 4, wherein the transducer comprises a non-invasive detecting element.

12. The sensor assembly according to claim 4, wherein the transducer comprises an invasive detecting element.

13. The sensor assembly according to claim 11, wherein there is no physical contact between the detecting element and the body surface of the mammal.

14. The sensor assembly according to claim 4, wherein the transducer comprises a detecting element selected from electrodes (polar, bipolar), a pressure sensor, a needle with an electrode, an accelerometer, a photo detector, a microphone, ISFET, an NTC resistor, a band gap detector, an ion membrane, an enzyme detector or a condenser.

15. The sensor assembly according to claim 4, wherein the transducer is capable of at least one of detecting a physiological condition, influencing a physiological condition, detecting a neurological condition, and influencing a neurological condition.

16. The sensor assembly according to claim 1, wherein the sensor assembly is capable of measuring electromyographic (EMG) signals, electrocardiographic (ECG) signals and electroencephalography (EEG) signals.

17. A multi-sensor network comprising one or more sensor assembly according to claim 1.

18. A multi-sensor network comprising at least two sensor assemblies according to claim 17 suitable for measuring heart rate.

19. A sensor assembly adapted to be attached to a body surface, comprising:
- a sensor circuit including a plurality of electrical components arranged on a printed circuit board, wherein the plurality of electrical components includes an antenna and a microprocessor, and wherein the sensor circuit having a proximal portion and a distal portion, the proximal portion of the sensor circuit configured to couple to the body surface;
- a housing containing at least the printed circuit board of the sensor circuit, the housing having a recess adapted to receive at least one power source for powering at least the antenna and the microprocessor of the sensor circuit, wherein the housing is formed of a proximal housing part and a distal housing part;
- the at least one power source, wherein the at least one power source is disposed within the recess of the housing;
- an adhesive device including at least one adhesive material for attaching the sensor assembly to the body surface, the adhesive device being adhesively coupled to, and contacting, the at least one power source in a first contact area and being adhesively coupled to, and contacting, the sensor circuit in a second contact area;
- wherein the adhesive coupling between the adhesive device and the power source resists greater pull force than does the adhesive coupling between the adhesive device and the sensor circuit; and
- wherein the adhesive device does not include electrical contacts.

* * * * *